United States Patent
Metzger et al.

(10) Patent No.: US 12,141,963 B2
(45) Date of Patent: Nov. 12, 2024

(54) SYSTEMS AND METHODS FOR IDENTIFYING BIOACTIVE AGENTS UTILIZING UNBIASED MACHINE LEARNING

(71) Applicant: THE ROCKEFELLER UNIVERSITY, New York, NY (US)

(72) Inventors: Jakob Metzger, New York, NY (US); Fred Etoc, New York, NY (US); Ali Brivanlou, New York, NY (US); Eric Siggia, New York, NY (US)

(73) Assignee: THE ROCKEFELLER UNIVERSITY, New York, NY (US)

( * ) Notice: Subject to any disclaimer, the term of this patent is extended or adjusted under 35 U.S.C. 154(b) by 704 days.

(21) Appl. No.: 17/282,039

(22) PCT Filed: Oct. 4, 2019

(86) PCT No.: PCT/US2019/054826
§ 371 (c)(1),
(2) Date: Apr. 1, 2021

(87) PCT Pub. No.: WO2020/072977
PCT Pub. Date: Apr. 9, 2020

(65) Prior Publication Data
US 2021/0372994 A1   Dec. 2, 2021

Related U.S. Application Data

(60) Provisional application No. 62/741,107, filed on Oct. 4, 2018.

(51) Int. Cl.
*G06T 7/62* (2017.01)
*C12N 5/0735* (2010.01)
(Continued)

(52) U.S. Cl.
CPC .......... *G06T 7/0012* (2013.01); *C12N 5/0606* (2013.01); *G01N 1/30* (2013.01);
(Continued)

(58) Field of Classification Search
CPC .......... G01N 1/30; G06N 3/084; G16B 40/00; G06T 5/002; G06T 5/10; G01J 3/2823;
(Continued)

(56) References Cited

U.S. PATENT DOCUMENTS

| | | | | |
|---|---|---|---|---|
| 6,463,438 B1 * | 10/2002 | Veltri | ................... | G06V 20/695 706/15 |
| 2005/0143628 A1 * | 6/2005 | Dai | ....................... | G01N 33/567 600/300 |

(Continued)

FOREIGN PATENT DOCUMENTS

| CN | 108280320 A | 7/2018 |
|---|---|---|
| WO | 2016/044681 A1 | 3/2016 |

OTHER PUBLICATIONS

Coudray, N., et al., "Classification and mutation prediction from non-small cell lung cancer histopathology images using deep learning", Nature Medicine, Nature Publishing Group US, NY, vol. 24, No. 10, Sep. 17, 2018, pp. 1559-1567.
(Continued)

*Primary Examiner* — Phuoc H Doan
(74) *Attorney, Agent, or Firm* — Hoffmann & Baron LLP

(57) ABSTRACT

Systems and methods for identifying molecules that are biologically active against a disease, where the method can comprise culturing a first mammalian cell population under organoid formation conditions in the presence of a test molecule to obtain a first organoid, wherein the first mammalian cell population, when cultured under the organoid formation conditions in the absence of the test molecule, results in an organoid with a disease phenotype; imaging the
(Continued)

first organoid following exposure to the test molecule; analyzing one or more images of the first organoid using a neural network that has been trained to assign a probability score of disease or non-disease ranging between 0% and 100%; assigning the first organoid a probability score ranging between 0% and 100%; wherein the test molecule is biologically active against the disease if the probability score of the first organoid is greater than a cutoff probability score of non-disease or lower than a cutoff probability score of disease.

23 Claims, 24 Drawing Sheets

(51) Int. Cl.
| | |
|---|---|
| *G01N 1/30* | (2006.01) |
| *G01N 33/50* | (2006.01) |
| *G06F 18/21* | (2023.01) |
| *G06F 18/214* | (2023.01) |
| *G06N 3/084* | (2023.01) |
| *G06T 7/00* | (2017.01) |
| *G06V 10/764* | (2022.01) |
| *G06V 10/82* | (2022.01) |
| *G06V 20/69* | (2022.01) |
| *G16B 40/00* | (2019.01) |

(52) U.S. Cl.
CPC ..... *G01N 33/5014* (2013.01); *G01N 33/5076* (2013.01); *G06F 18/214* (2023.01); *G06F 18/217* (2023.01); *G06N 3/084* (2013.01); *G06V 10/764* (2022.01); *G06V 10/82* (2022.01); *G06V 20/698* (2022.01); *G16B 40/00* (2019.02); *C12N 2503/02* (2013.01); *C12N 2510/00* (2013.01); *G06T 2200/04* (2013.01); *G06T 2207/20076* (2013.01); *G06T 2207/20081* (2013.01); *G06T 2207/20084* (2013.01); *G06T 2207/30024* (2013.01); *G06T 2207/30072* (2013.01); *G06V 2201/03* (2022.01)

(58) Field of Classification Search
CPC .... C12N 7/00; A61K 39/145; G06V 10/7747; G16C 20/70
See application file for complete search history.

(56) References Cited

U.S. PATENT DOCUMENTS

| | | |
|---|---|---|
| 2013/0058925 A1 | 3/2013 | Dinney et al. |
| 2014/0336358 A1 | 11/2014 | Darnell |
| 2015/0213599 A1 | 7/2015 | Buzaglo et al. |
| 2016/0186146 A1 | 6/2016 | Thomson et al. |
| 2017/0191030 A1 | 7/2017 | Ortega et al. |
| 2018/0211380 A1 | 7/2018 | Tandon et al. |
| 2020/0150022 A1 | 5/2020 | Ugawa et al. |
| 2020/0357489 A1 | 11/2020 | Cheng et al. |

OTHER PUBLICATIONS

Liang, Z., et al., "CNN-based image analysis for malaria diagnosis", 2016 IEEE International Conference on Bioinformatics and Biomedicine (BIBM), IEEE, Dec. 15, 2016, pp. 493-496.

Kobayashi, H., et al., "Label-free detection of cellular drug responses by high-throughput bright-field imaging and machine learning", Scientific Reports, vol. 7, No. 1, Sep. 29, 2017, pp. 1-9.

Bejnordi, B. E. et al., "Using deep convolutional neural networks to identify and classify tumor-associated stroma in diagnostic breast biopsies", Modern Pathology, Nature Publishing Group, GB, vol. 31, No. 10, Jun. 13, 2018, pp. 1502-1512.

* cited by examiner

FIG. 6B

SYSTEMS AND METHODS FOR IDENTIFYING BIOACTIVE AGENTS UTILIZING UNBIASED MACHINE LEARNING

CROSS REFERENCE TO RELATED APPLICATIONS

The present application is a national stage application which claims priority from PCT Application No. PCT/US2019/054826 filed Oct. 4, 2019, which in turn, claims priority from U.S. Provisional Application Ser. No. 62/741,107 filed Oct. 4, 2018. Applicant claims the benefits of 35 U.S.C. § 120 as to the PCT application and priority under 35 U.S.C. § 119 as to the said U.S. Provisional application, and the entire disclosures of all applications are incorporated herein by reference in their entireties.

1. STATEMENT REGARDING FEDERALLY SPONSORED RESEARCH

This invention was made with government support under NIHR01GM101653 awarded by National Institutes of Health and STTR grant awarded by National Science Foundation. The government has certain rights in the invention.

2. BACKGROUND

Differentiating stem cells in vitro can reveal the intrinsic potential of stem cells to self-organize into organoids. In theory, organoids hold great promise for disease modeling in vitro and for use as a tool for testing potential therapeutics. However, the inherent heterogeneity of those large, multicellular structures requires new quantification tools that can fully harness their biological complexity and translate it into useful therapeutic predictions.

The fact that organoids show a stereotypical organization allows, in principle, for phenotypic differences between "wild type" ("WT" or "non-disease") and a counterpart "disease" organoid to be recognized and quantified. The organoids can then be screened for pharmacological compounds that revert the disease phenotype to the WT.

Downstream of such a screen on organoids, an ideal analytical scheme would quantify, for each compound, two quantities that are relevant for translating hit compounds to the clinic. First, the therapeutic potential needs to be accurately determined. Second, adverse, potential off target effects and cellular toxicity are ideally quantified, as early rejection of toxic compounds will prevent failure in clinical trials, saving large and useless investments.

3. SUMMARY

This disclosure provides artificial neural networks that can be used in methods for identifying test molecules that are biologically active against a disease and/or quantifying the potential toxicity of test molecules. Features of exemplary neural networks are described in Section 5.2 and the numbered embodiments set forth in Section 7.

In some embodiments, the neural networks can learn the differences between non-disease and disease phenotypes. The weights of the artificial neurons can be pre-trained on a large number of images from a database of images, for example the ImageNet database, which has millions of images. A pre-trained network can then be trained on images from non-disease and disease organoids to lean the best combination of image features from the different available channels to identify optimal, unbiased non-disease and disease fingerprints. Training can be performed on graphics processing units (GPUs) and even a deep network with many layers can be trained in only minutes to a few hours depending on the size, number and difficulty of the training. After training, application of a trained network of the disclosure to unseen images is generally very fast, e.g., thousands of images can be analyzed in seconds.

The disclosure further provides methods for identifying test molecules that are biologically active against a disease and/or quantifying the potential toxicity of test molecules.

In one aspect, the disclosure provides methods for identifying a molecule that is biologically active against a disease comprising culturing a mammalian cell population under organoid formation conditions in the presence of a test molecule to obtain an organoid, wherein the mammalian cell population cultured under organoid formation conditions in the absence of a biologically active molecule results in an organoid with a disease phenotype; imaging the organoid; analyzing one or more images of the organoid using a neural network that has been trained to assign a probability score of disease or non-disease ranging between 0% and 100%; and assigning the organoid a probability score ranging between 0% and 100%. Probability scores can alternatively range from 0 to 1, 0 to 10, or any arbitrary range. The test molecule can be considered biologically active against the disease if the probability score of the organoid is greater than a cutoff probability score of non-disease or lower than a cutoff probability score of disease. Exemplary methods for identifying molecules that are biologically active against a disease are described in Sections 5.2.5 and 5.3 and numbered embodiments 1 to 122.

Advantageously, various embodiments of the neural networks and methods of the disclosure can use available differences between disease and WT in an optimal way. First, the therapeutic potential of test molecules can be measured as defined by the degree of phenotypic reversal. Additionally, a classifier that can recognize WT and disease phenotypes can allow for the definition of a third class corresponding to a toxic phenotype, without the need to specify beforehand how the toxic phenotype may look. This class can contain organoids that react to treatment by test molecules, but in a way that does not revert the phenotype to WT. This third class generally includes compounds that will likely have adverse effects in vivo. Thus, in some embodiments, the methods of the disclosure comprise or further comprise using a neural network of the disclosure to assign a probability score of toxicity or non-toxicity to an organoid treated with a test compound ranging between 0% and 100% (or 0 to 1, 0 to 10, or any arbitrary range). Exemplary methods for assigning a probability score of toxicity or non-toxicity are described in Sections 5.2.6 and 5.3 and numbered embodiments 1 to 122.

The disclosure further provides systems comprising a processor and a non-transient storage medium (e.g., a hard disk, flash drive, CD or DVD) including processor executable instructions for implementing the analysis and/or assigning steps of the methods of the disclosure. The systems can further comprise an imaging device capable of imaging an organoid (e.g., a microscope having a camera). Exemplary systems are described in numbered embodiments 1 to 122.

The disclosure further provides methods of training neural networks to analyze images of organoids and assign a probability score of disease or non-disease. Exemplary methods are described in Section 5.2.4 and numbered embodiments 1 to 122.

4. BRIEF DESCRIPTION OF THE FIGURES

FIG. 1 illustrates the structure of an exemplary neural network of the disclosure.

FIGS. 2A-2C are flow charts illustrating aspects of training exemplary neural networks of the disclosure and their use to analyze the therapeutic potential and toxicity of test compounds. FIG. 2A is a flow chart showing exemplary steps for training a neural network. FIG. 2B is a flow chart showing exemplary steps for analyzing the therapeutic potential of test molecules. FIG. 2C is a flow chart showing exemplary steps for analyzing both the therapeutic potential and toxicity of test molecules.

FIGS. 3A-3E show immunofluorescence analyses of HD model organoids. FIG. 3A: Side view: DAPI, PAX6 (green), and N-CAD (orange). FIG. 3B: Top view: DAPI, neural marker PAX6 (green), neural crest marker SOX10 (red), and cranial placode marker SIX1 (yellow). FIG. 3C: Side view including non-neural ectoderm maker TFAP2A (blue). Epidermis cells are TFAP2A+ only. All scale bars represent 50 µm. FIG. 3D: cartoon representation of a human embryo at gastrulation. FIG. 3E: cartoon representation of a human HD model organoid.

FIGS. 4A-4B show phenotypic signatures of Huntington's disease (HD) cell lines. FIG. 4A: Representative images of PAX6 area for the different HD isogenic lines in a HD model organoid assay. PAX6 staining allows visualization of the Pax6 area. FIG. 4B: Associated quantification of PAX6 area normalized by the colony area.

FIGS. 5A-5C show adaptation of the HD model organoid phenotype to 96-well plates. FIG. 5A: PAX6 staining in a well with WT HD model organoid. FIG. 5B: PAX6 staining in a well with HD model organoid. FIG. 5C: Quantification by threshold-based segmentation of the PAX6+ areas in the two different genetic backgrounds in multiple wells of two independent 96-well plates.

FIGS. 6A-6B show measurement of the assay Z' factor in Example 1. FIG. 6A: Measure of the PAX6+ area by segmentation in a WT/20CAG control plate (left) or in a HD/56CAG control plate (right). Each well is color-coded according to its mean PAX6 area. FIG. 6B: Calculation of the well-to-well Z' factor. Each well is color-coded with its Z' factor and the associated value is reported.

FIGS. 7A-7B illustrate machine learning assisted phenotypic analysis. FIG. 7A: Training of an exemplary network for optimal recognition of wild type and disease phenotypes. FIG. 7B: Illustration of quantification of phenotype reversal. Adding drug 1 to the diseased phenotype: (bottom) the network now gives a higher chance to belonging to the wild type class than without the drug (top).

FIGS. 8A-8B show machine learning assisted phenotypic analysis. FIG. 8A: Example of images from the different genetic backgrounds: WT (RUES2), Htt-/-, and Htt-/- with Htt over-expression. The network was trained for recognition of WT (RUES2) and Htt-/- images. FIG. 8B: The network was queried for classification of images it never saw before and, for each image, the network assigned a probability, $p_{wt}$. A value of 1 means that the image was classified as WT and a value of 0 means that it was classified as Htt-/-. WT and KO images were accurately classified. Images from the rescue over-expression experiment showed higher probability of belonging to the WT.

FIG. 9 shows percentages of correctly and incorrectly identified 20CAG (WT) and 56CAG (disease) images. Total number of validation images: 754 (WT) and 692 (disease).

FIGS. 10A-10B show rescue of the Z' factor by neural network assisted phenotypic analysis. FIG. 10A: Comparison of the Z' factor calculated using the regular segmentation scheme (black circles) or the machine learning toolbox (crosses). All wells showed Z'>0 with the machine learning toolbox. FIG. 10B: Distribution of the Z' score coming from the machine learning-based analysis.

Figure 13:
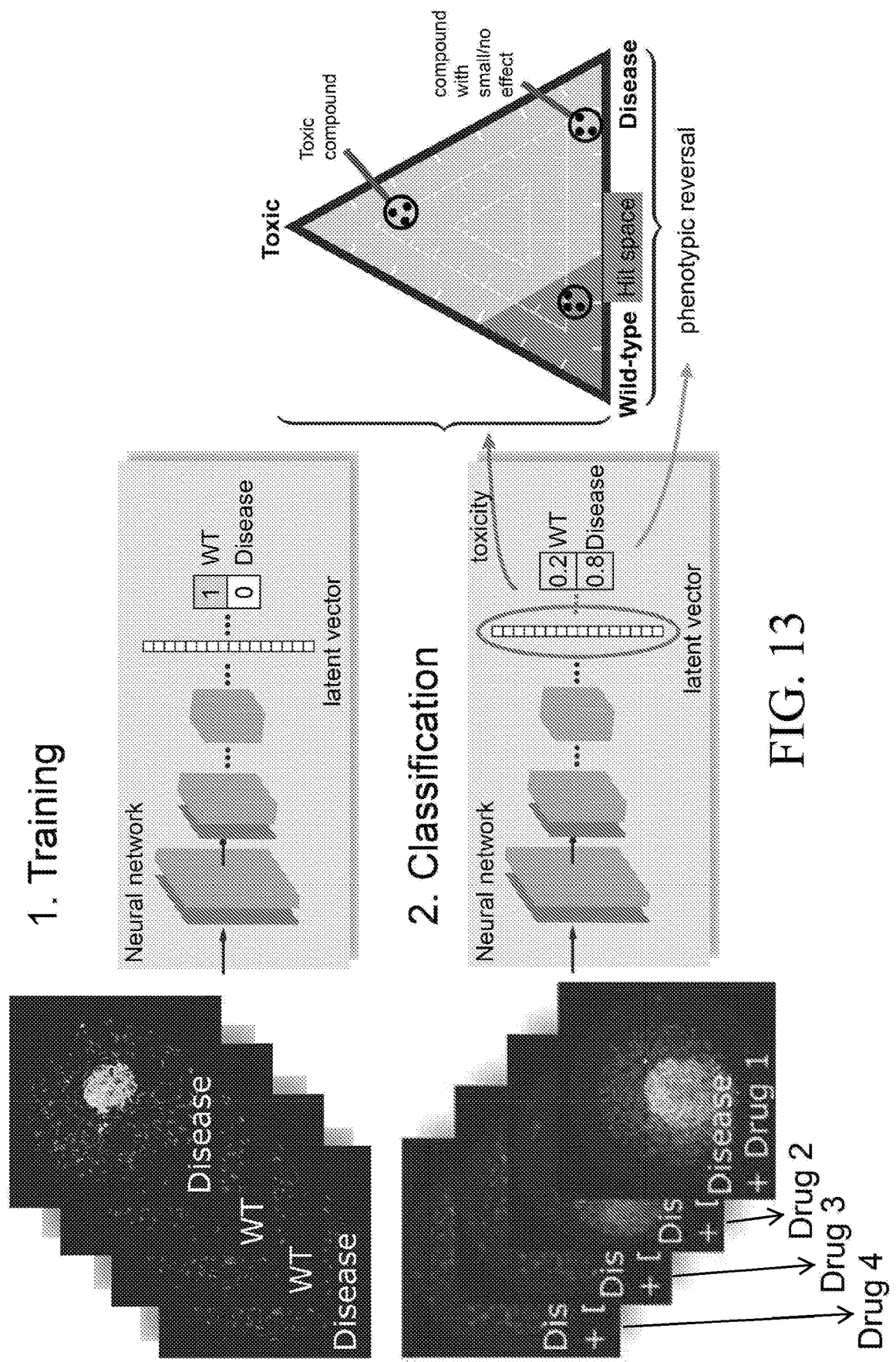

FIG. 13 Illustrates exemplary neural network training and classification of compounds. The final prediction of an exemplary network, WT vs. disease, quantifies the amount of phenotypic reversal of the drug. The latent vector before the final classification can be used to define a distance to both WT and disease, which can be used as a measure of toxicity.

Figure 14:
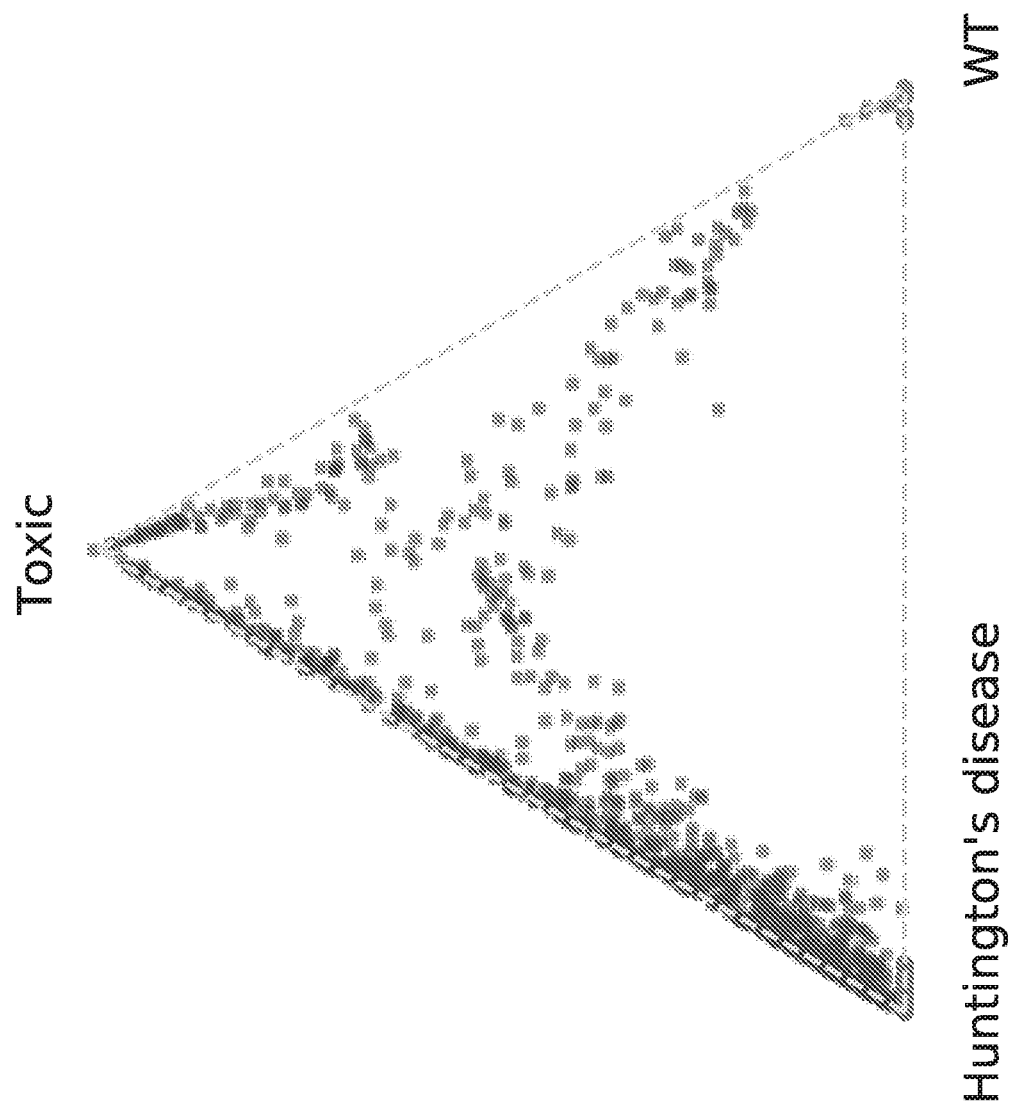

FIG. 14 shows the result of a screen for phenotypic reversal using neurulation organoids derived from stem cells carrying a mutation for Huntington's disease. Each data point represents one well with approximately 25 organoids. Green points correspond to untreated control wells, orange are wild type control wells. Five compounds are close to the wild type (WT) corner showing that they successfully revert the disease phenotype to WT.

Figure 15:
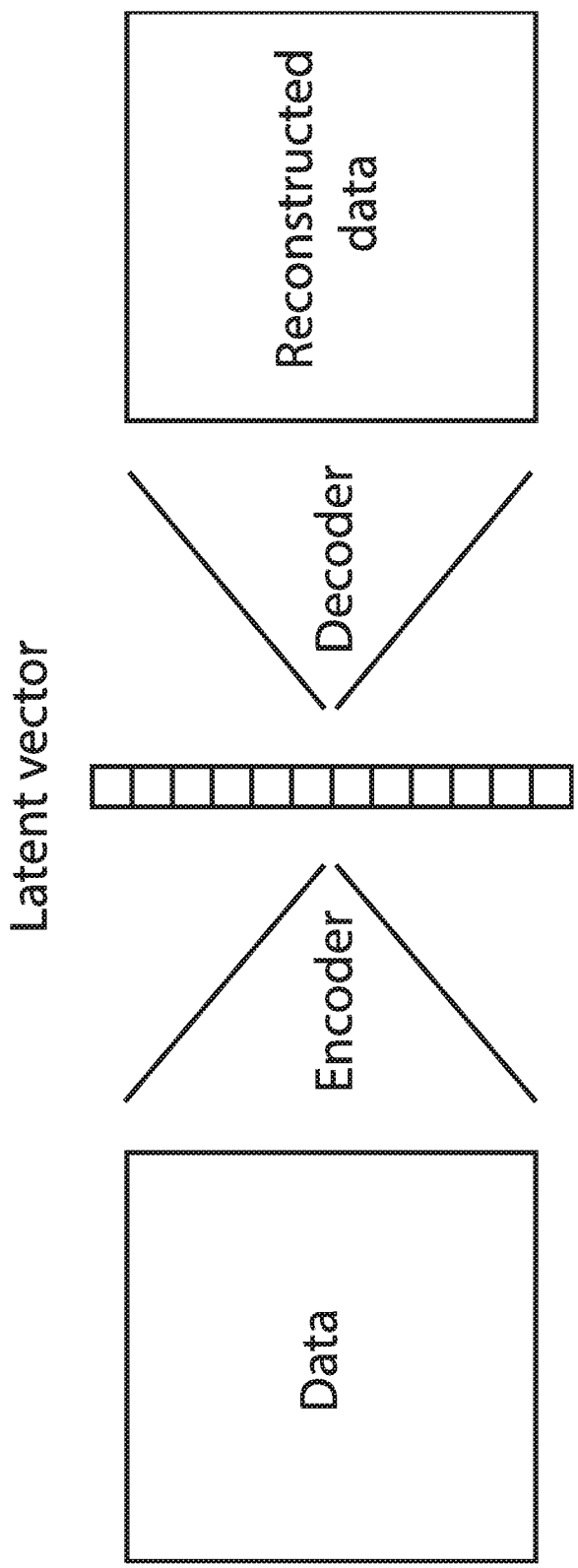

FIG. 15 Depicts an example of an autoencoder. The encoder and decoder neural networks are trained such that the reconstructed data matches the input data as closely as possible, resulting in a low-dimensional representation of the data in the latent space.

Figure 16:
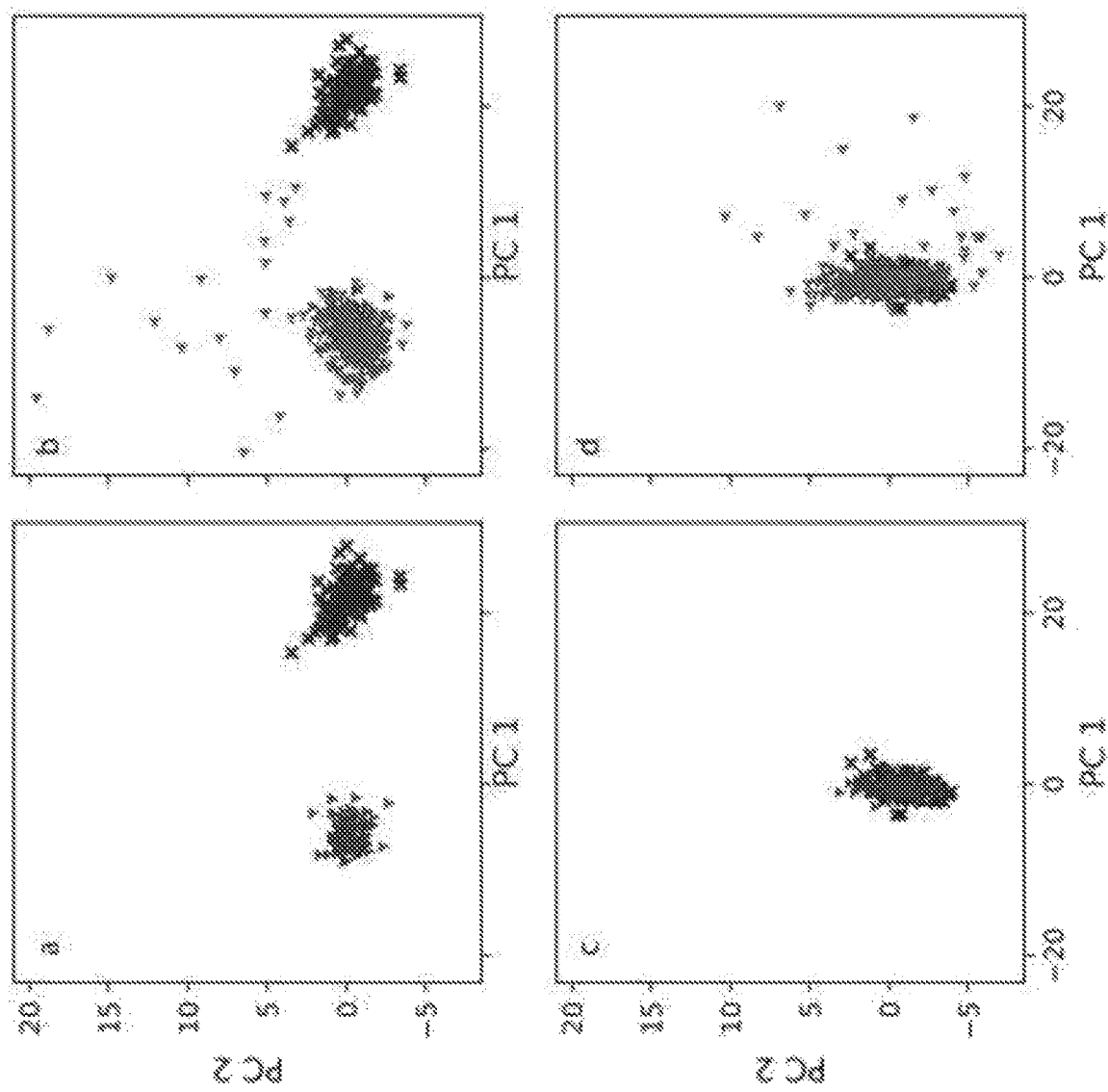

FIG. 16 Depicts a visualization of latent vectors. (a) Principal component analysis (PCA) of the latent vectors of wild type (WT) and disease images, displayed are the first two principal components (PC 1, PC 2). (b) Same vectors with a set of compounds superimposed. (c) Same vectors as in (a) but with the variation between WT and disease removed. (d) Same vectors as (b) but with the variation between WT and disease removed.

Figure 17:
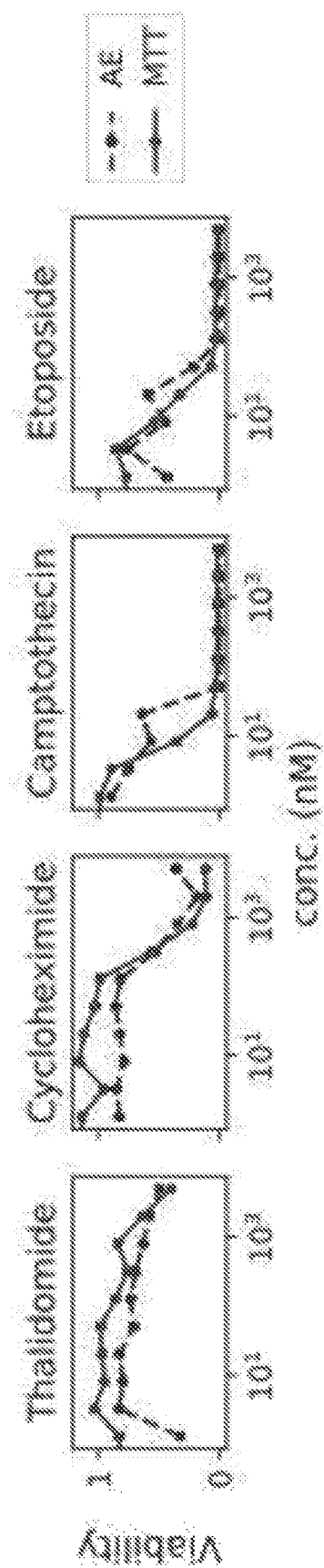

FIG. 17 Depicts cell viability as determined by a method as described herein (autoencoder, "AE") and the conventional "MTT" assay for different drugs and concentrations.

5. DETAILED DESCRIPTION

This disclosure provides artificial neural networks that can be used to identify test molecules that are biologically active against a disease and/or to quantify the potential toxicity of test molecules. Exemplary neural networks are described in Section 5.2 and the numbered embodiments set forth in Section 7.

In one aspect, the method for classifying a test organoid comprises the steps of: imaging a test organoid to provide an organoid image; analyzing the organoid image with a trained neural network that has been trained to assign a classification to the test organoid, wherein the classification comprises disease phenotype or non-disease phenotype. Exemplary methods for classifying a test organoid are described in Sections 5.2.3 to 5.2.5 and numbered embodiments 1 to 26.

In one aspect, the method for identifying a molecule that is biologically active against a disease comprises culturing a mammalian cell population under organoid formation conditions in the presence of a test molecule to obtain an organoid, wherein the mammalian cell population cultured under organoid formation conditions in the absence of the test molecule results in an organoid with a disease phenotype; imaging the organoid; analyzing one or more images of the organoid using a neural network that has been trained to assign a probability score of disease or non-disease ranging between 0% and 100%; and assigning the organoid a probability score ranging between 0% and 100%. The test molecule can be considered biologically active against the disease if the probability score of the organoid is greater than a cutoff probability score of non-disease or lower than a cutoff probability score of disease. Exemplary methods for identifying molecules that are biologically active against a disease are described in Sections 5.2.5 and 5.3 and numbered embodiments 27 to 121.

In some embodiments, the methods of the disclosure comprise or further comprise assigning a probability score of toxicity or non-toxicity to an organoid treated with a test compound ranging between 0% and 100% (or 0 to 1, 0 to 10, or any arbitrary range). Exemplary methods for assigning a probability score of toxicity or non-toxicity are described in Sections 5.2.6 and 5.3 and numbered embodiments 122 to 136.

The disclosure further provides non-transient storage media (e.g., a hard disk, flash drive, CD or DVD) including processor executable instructions for implementing the analysis and assigning steps of the methods of the disclosure, and systems comprising such a non-transient storage medium and a processor. The systems can further comprise an imaging device capable of imaging an organoid (e.g., a microscope having a camera). Exemplary systems are described in numbered embodiments 140 and 141.

The disclosure further provides methods of training neural networks to analyze images of organoids and assign a probability score of disease or non-disease. Exemplary methods are described in Section 5.2.4 and numbered embodiments 142 to 159.

5.1. Definitions

Unless defined otherwise herein, all technical and scientific terms used herein have the same meaning as commonly understood by one of ordinary skill in the art. Various scientific dictionaries that include the terms included herein are well known and available to those in the art. Any methods and materials similar or equivalent to those described herein find use in the practice of the embodiments disclosed herein.

The terms defined immediately below are more fully understood by reference to the specification as a whole. The definitions are for the purpose of describing particular embodiments only and aiding in understanding the complex concepts described in this specification. They are not intended to limit the full scope of the disclosure. Specifically, it is to be understood that this disclosure is not limited to the particular sequences, compositions, algorithms, systems, methodology, protocols, and reagents described, as these may vary, depending upon the context they are used by those of skill in the art.

As used in this specification and appended claims, the singular forms "a", "an", and "the" include plural referents unless the content and context clearly dictates otherwise. Thus, for example, reference to "a device" includes a combination of two or more such devices, and the like.

Unless indicated otherwise, an "or" conjunction is intended to be used in its correct sense as a Boolean logical operator, encompassing both the selection of features in the alternative (A or B, where the selection of A is mutually exclusive from B) and the selection of features in conjunction (A or B, where both A and B are selected). In some places in the text, the term "and/or" is used for the same purpose, which shall not be construed to imply that "or" is used with reference to mutually exclusive alternatives.

Throughout this specification, quantities are defined by ranges, and by lower and upper boundaries of ranges. Each lower boundary can be combined with each upper boundary to define a range. The lower and upper boundaries should each be taken as a separate element.

The term "organoid" refers to a cell or tissue culture forming a heterogeneous 3D agglomeration of cells that recapitulates aspects of cellular self-organization, architecture and signaling interactions present in the native organ. The term "organoid" includes spheroids or cell clusters formed from suspension cell cultures as well as stem cells differentiated on micropatterns.

The term "spheroid" refers to an aggregate or assembly of cells cultured to allow 3D growth as opposed to growth as a monolayer. It is noted that the term "spheroid" does not imply that the aggregate is a geometric sphere. The aggregate may be highly organized with a well defined morphology or it may be an unorganized mass; it may include a single cell type or more than one cell type.

The term "micropattern" refers to a pattern having features on the microscale. For example, a micropattern can include repeating circles or spheres having a diameter on the micrometer scale, or a micropattern can include repeating lines having line widths on the micrometer scale, or a micropattern can include repeating units, e.g., squares, triangles, diamonds, rhomboids, or other two- or three-dimensional geometric shapes, said shapes having at least one feature, e.g., height, width, length, etc. on the micrometer scale. Other micropatterns are contemplated for use in the methods of the disclosure and can include free-form shapes and/or geometries, etc. Micropatterns can be generated using art-recognized micro-patterning techniques including, but not limited to lithography, stenciling, etching, and the like.

The term "marker" or "biomarker" refers generally to a DNA, RNA, protein, carbohydrate, or glycolipid-based molecular marker, the expression or presence of which in a cultured cell population can be detected by standard methods (or methods disclosed herein) and is consistent with one or more cells in the cultured cell population being a particular type of cell. The marker may be a polypeptide expressed by the cell or an identifiable physical location on a chromosome, such as a gene, a restriction endonuclease recognition site or a nucleic acid encoding a polypeptide (e.g., an mRNA) expressed by the native cell. The marker may be an expressed region of a gene referred to as a "gene expression marker", or some segment of DNA with no known coding function. The biomarkers may be cell-derived, e.g., secreted, products.

"Screening" refers to the process in which one or more properties of one or more molecules are determined. For example, typical screening processes include those in which one or more properties of one or more molecules that are members of one or more libraries are determined.

A "library" refers to a collection of at least two different molecules, such as small molecule compounds, proteins, peptides, or nucleic acids. For example, a library typically includes at least about 10 different molecules. Large libraries typically include at least about 100 different molecules, more typically at least about 1,000 different molecules. For some applications, the library includes at least about 10,000 or more different molecules.

"Selection" refers to the process in which one or more molecules are identified as having one or more properties of interest. Thus, for example, one can screen a library to determine one or more properties of one or more library members, such as reversion of a disease phenotype to a WT (non-disease) phenotype or toxicity. If one or more of the library members is/are identified as possessing a property of interest (e.g., reversion of a disease phenotype to a WT phenotype), it is selected. Selection can include the isolation of a library member and further testing, e.g., in an animal model. Further, selection and screening can be, and often are, simultaneous.

The term "extracellular matrix components" refers to molecules or materials, whether natural or synthetic, that function as substrates for cell attachment and growth. Examples of extracellular matrix components include, without limitation, collagen, laminin, fibronectin, vitronectin, elastin, glycosaminoglycans, proteoglycans, and combinations of some or all of these components (e.g., MATRIGEL™, Collaborative Research, Catalog No. 40234).

The term "tissue attachment surfaces" refers to surfaces having a texture, charge or coating to which cells may adhere in vitro. Examples of attachment surfaces include, without limitation, stainless steel wire, VELCRO™, suturing material, native tendon, covalently modified plastics (e.g., RGD complex), and silicon rubber tubing having a textured surface.

"Training set" refers to a set of images that one or more models are fitted to and built upon. For instance, for an organoid phenotype model, a training set comprises images of non-disease and disease organoids, which are optionally stained with one or more markers as described in Section 5.2.4, infra.

5.2. Neural Networks 5.2.1. Network Architecture

Artificial neural networks (ANNs) are processing devices (algorithms or actual hardware) that are loosely modeled after the neuronal structure of the mammalian cerebral cortex but on much smaller scales. A basic unit of computation in the ANN is the neuron. As used herein, the term "neuron" is used interchangeably with the term "node". A large ANN might have hundreds or thousands or millions of neurons.

Figure 1:
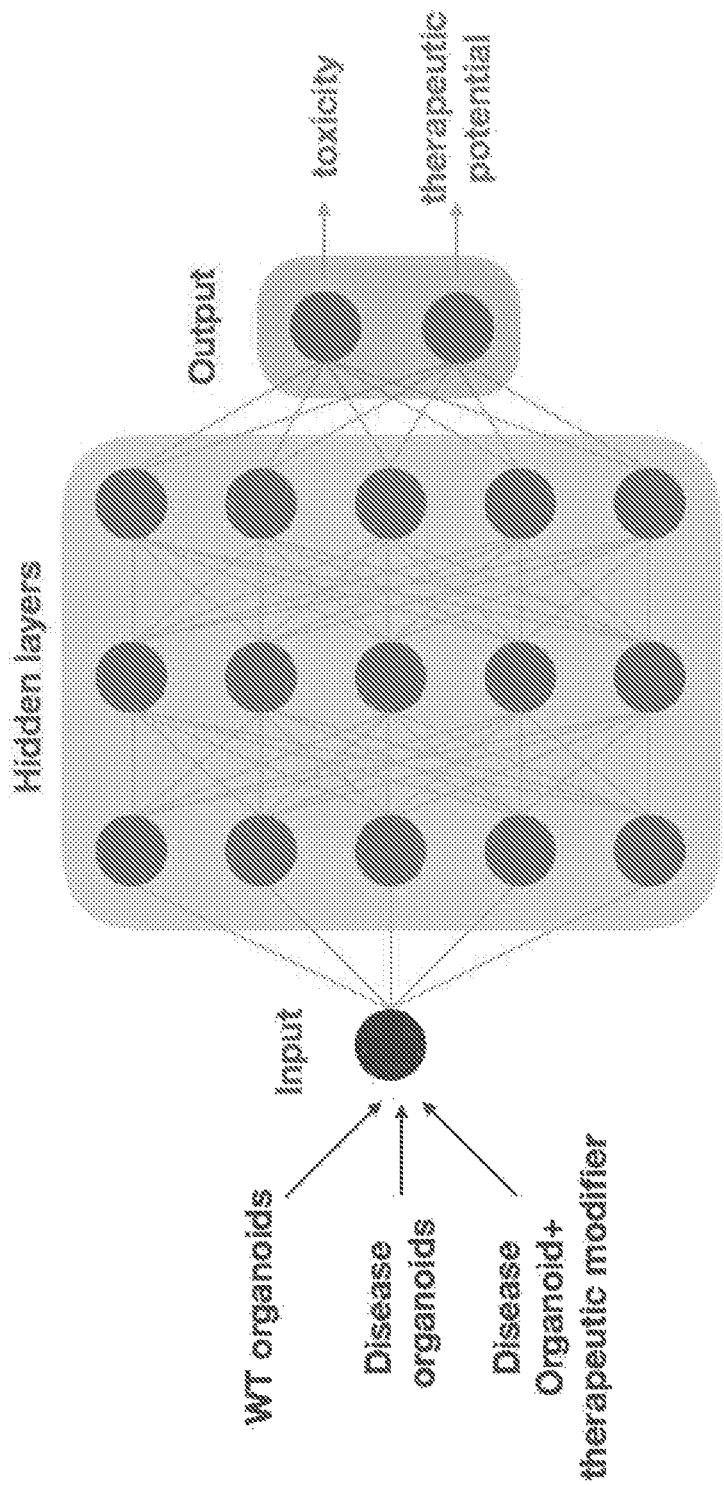

Neural networks are typically organized in layers. Layers are made up of a number of interconnected "nodes" which contain an "activation function." Patterns are presented to the network via the "input layer," which communicates to one or more "hidden layers" where the actual processing is done via a system of weighted "connections". As used herein, the term "hidden layers" are used interchangeably with the term "latent layers". The hidden layers then link to an "output layer" where the answer is output, as illustrated for an exemplary network in FIG. 1.

Neural networks of the disclosure can be coded using a machine-learning framework such as PyTorch or TensorFlow.

5.2.2. Convolutional Neural Networks

Convolutional neural networks (ConvNets or CNNs) are a type of ANNs used for image recognition and classification. CNN image classifications take an input image, process it and classify it under a category, eliminating the need for manual feature extraction. Because computers see an input image as array of pixels, the image resolution will determine the type of matrix array (in h×w×d, where h=Height, w=Width, d=Dimension) a computer will process an image into. For example, an image of 6×6×3 array of matrix of RGB (3 refers to RGB values) and an image of 4×4×1 array of matrix of grayscale image.

A CNN can have tens or hundreds of layers that each learn to detect different features of an image. A CNN can be trained by showing a set of training images to the CNN. Filters can be applied to each training image at different resolutions, and the output of each convolved image is used as the input to the next layer. The filters can start as very simple features, such as brightness and edges, and increase in complexity to features that uniquely define the object.

Like other neural networks, a CNN is composed of an input layer, an output layer, and generally many hidden layers in between. These layers perform operations that alter the data with the intent of learning features specific to the data. Three of the most common layers are convolution, activation or ReLU, and pooling.

When performing training and analysis with deep learning CNNs, each input image will generally pass through a series of convolution layers with filters (kernels), pooling, and fully connected layers (FC), with a final softmax function to classify an object with probabilistic values between 0 and 1 (or 0% to 100%, 0 to 10, or any arbitrary range).

5.2.2.1. Convolution Layer

Convolution is the first layer to extract features from an input image. Convolution preserves the relationship between pixels by learning image features using small squares of input data. It is a mathematical operation that takes two inputs such as image matrix and a filter or kernel. Convolution of an image with different filters can perform operations such as edge detection, blur and sharpen by applying filters.

5.2.2.2. Strides

Stride is the number of pixels shifts over the input matrix. When the stride is 1 the filters are moved 1 pixel at a time. When the stride is 2 the filters are moved 2 pixels at a time and so on.

5.2.2.3. Padding

Sometimes a filter does not perfectly fit the input image. The picture can then be padded with zeros (zero-padding) so that it fits, or the part of the image where the filter did not fit can be dropped. The latter is called valid padding which keeps only the valid part of the image.

5.2.2.4. Non-Linearity (ReLU)

ReLU stands for Rectified Linear Unit for a non-linear operation. The output is $f(x)=\max(0,x)$. ReLU's purpose is to introduce non-linearity in the ConvNet in order for the ConvNet to learn non-linear relations between the input images and the classification. There are other non linear functions such as tan h or sigmoid that can also be used instead of ReLU. ReLU is preferred since performance-wise ReLU is better than the other two.

5.2.2.5. Pooling Layer

Pooling layers can reduce the number of parameters when the images are too large. Spatial pooling (also called subsampling or downsampling) reduces the dimensionality of each map but retains the important information. Spatial pooling can be of different types such as max pooling, average pooling, or sum pooling. Max pooling takes the largest element from the rectified feature map. An average pooling layer performs down-sampling by dividing the input into rectangular pooling regions and computing the average values of each region. The sum of all elements in the feature map is called sum pooling.

5.2.2.6. Fully Connected Layer

A fully connected layer takes all neurons in the previous layer and connects them to every single neuron it has. In a fully connected layer, a matrix can be flattened into vectors and fed into a fully connected layer like neural network. A neural network of the disclosure can have more than one fully connected layer. With the fully connected layers, features can be combined together to create a model. An activation function such as softmax or sigmoid can be used to classify the outputs, e.g., as wild-type (non-diseased) or diseased.

5.2.3. Neural Networks for Analyzing Non-Disease and Disease Organoids

Pre-trained convolutional networks are usually considerably more efficient than untrained networks and therefore in some embodiments pre-trained networks are used for making a neural network for classifying images from organoids having a non-disease or disease phenotype. For 2D images, frameworks providing convolutional NNs pre-trained on the ImageNet database are commercially available (e.g., ResNet, DenseNet, or VGG16). For 3D images, NNs pretrained on the Kinetics dataset are commercially available (e.g., ResNet or DenseNet). Pretraining can be done on databases other than ImageNet or Kinetics, but ImageNet and Kinetics provide a very large and comprehensive dataset of images. Other network architectures can also be used, but convolutional networks excel at classifying images and are preferred.

Residual Networks (ResNets), a subclass of convolutional networks, are particularly efficient at classifying images. In some embodiments, a ResNet of 18 to 152 layers is used in the systems and methods of the disclosure. Pre-trained ResNets of different depths (with 18, 34, 50, 101 or 152 layers) are available in major machine-learning frameworks (e.g., ResNet18, ResNet34, ResNet50, ResNet101, or ResNet152). They can include blocks of layers made up of convolutional, Batch Normalization (BatchNorm) and Rectified Linear (ReLU) layers. A final Average Pooling and densely connected layer provided in a pre-trained ResNet can be removed and replaced by custom layers as described herein. Convolutional layers can be used to convolve a 3 by 3 pixel block of the input image with filters that are learned during the training process. The ReLU are nonlinear activation layers that can be used to apply the function $f(x) = \max(0,x)$ to all the inputs. This introduces nonlinearities to the network that are required for learning nonlinear relationships between images and classification. BatchNorm layers can be used to normalize the network activations, which can improve stability and allow for more efficient training.

The last layers of a NN are generally more specific to the dataset than the initial layers and, therefore, the last Average Pooling and fully connected layer of an off-the shelf pre-trained network can be removed and replaced with some or all of untrained Adaptive Average Pooling, Adaptive Maximum Pooling, Batch Norm, and Dropout layers in addition to fully connected layers, followed by a final softmax operation to classify images from organoids having a non-disease or disease phenotype. Preferably, the neural network includes Adaptive Average Pooling, Adaptive Maximum Pooling, Batch Norm, and Dropout layers, although embodiments in which some of the layers, such as Batch Norm and/or Dropout, are omitted are also contemplated. The pooling layers reduce the spatial size of the representation, dropout layers can avoid overfitting, and the fully connected layers have access to and bring together all activations of the previous layer (this is the default for a final layer in a classification network). In a preferred embodiment, a fully connected layer of 512 neurons is used, and directly afterwards the final fully-connected layer consists of only two neurons, one each for non-disease and disease. A final softmax can be used to convert the activation of these neurons into probabilities that sum to 1.

5.2.4. Training

Most ANNs contain some form of "learning rule" that modifies the weights of the connections according to the input patterns that it is presented with.

There are many different kinds of learning rules used by neural networks, one of which is called the delta rule. The delta rule is often utilized by the most common class of ANNs called "backpropagational neural networks" (BPNNs). Backpropagation is an abbreviation for the backwards propagation of error.

With the delta rule, as with other types of backpropagation, "learning" is a supervised process that occurs with each cycle (also called an "epoch") through a forward activation flow of outputs, and the backwards error propagation of weight adjustments. More simply, when a neural network is initially presented with a pattern it makes a random "guess" as to what it might be. It then sees how far its answer was from the actual one and makes an appropriate adjustment to its connection weights.

Within each hidden layer node is a sigmoidal activation function that introduces a non-linearity.

Backpropagation performs a gradient descent within the solution's vector space towards a "global minimum" along the steepest vector of the error surface. The global minimum is that theoretical solution with the lowest possible error. In most problems, the solution space is quite irregular with numerous "pits" and "hills" that may cause the network to settle down in a "local minimum" which is not the best overall solution.

Since the nature of the error space cannot be known a priori, neural network analysis often requires a large number of individual runs to determine the best solution. Learning rules generally have built-in mathematical terms to assist in this process which control the "speed" (β-coefficient) and the "momentum" of the learning. The speed of learning is actually the rate of convergence between the current solution and the global minimum. Momentum helps the network to overcome obstacles (local minima) in the error surface and settle down at or near the global minimum.

It is possible to over-train a neural network, which means that the network has been trained exactly to respond to only one type of input. Overtrained networks are not useful because they do not perform well on new input.

The neural networks of the disclosure can be trained using a set of non-disease and disease organoid images (which are preferably multichannel) split into training (e.g., 70%) and validation (e.g., 30%) images. Preferably, the training images comprise at least 300 non-disease and 300 disease images (e.g., 300 to 2000 images each, 300 to 1500 images each, 300 to 1000 images each, or 300 to 500 images each), or more. Images can be 2D images or 3D images. A neural network (NN) can then be trained on the training data set.

Images in the training set can include images of organoids stained for one or more markers such as organelle markers, cell differentiation markers, cell compartment markers, or combinations thereof. The one or more markers preferably includes one or more markers that highlight the gross morphology of the organoid and/or a specific population of cells contained in the organoid. Exemplary staining reagents include nuclear stains (e.g., DAPI and Hoechst nuclear stains), BrdU, calcein green, membrane dyes such as DiI, DiO, DiD, and DiR, Golgi staining reagents such as fluorescently labeled antibodies to GM130, ER staining reagents such as ER-Tracker™ Green (Cell Signaling Technology), phalloidin, and fluorescently labeled antibodies to N-Cadherin, E-Cadherin, ZO-1, and collagen.

Reagents specific to specific types of organoids or types of differentiated cells can also be used. For example, reagents for staining neurofilaments or nestin (e.g., fluorescently labeled antibodies) can be used to stain brain organoids; PAX6 staining reagents can be used to stain neural populations of cells; and SOX10 staining reagents can be used to stain neural crest cells.

Training can be performed by showing images to the network, comparing the output probabilities of WT or disease to the true value, and changing the network weights such that the next time the image is shown to the network, the network would give a prediction that is closer to the true value. Preferably, images are shown to the network during training in a random order. The fitting procedure is performed using the backpropagation algorithm, which is implemented in major neural network frameworks. The images are shown to the network many times, for example 200 to 800 times, 300 to 700 times, or 400 to 600 times (e.g., about 200 times, about 300 times, about 400 times, about 500 times, about 600 times, about 700 times). Images are "augmented" by applying a set of image transformations to each image that does not significantly change the content of the image but enlarges the pool of images that the network can learn from. Data augmentation operations can include some or all of the following (e.g., one, two, three, or all four): rotations, cropping, scaling the image from 90-110%, and changing the contrast of the images. Training can be done several times with different hyperparameters (number of layers, momentum and learning rate, dropout percentage, number of epochs) to find an optimal set of these parameters. In some embodiments, the hyperparameters comprise a combination of two, three, or four of the following: number of layers, momentum and learning rate, dropout percentage, and number of epochs.

Data augmentation and dropout are two strategies for avoiding overfitting. Over- and underfitting can be tested for by comparing the performance of the network on the training and validation set. If the training accuracy is higher than the validation accuracy, the network is overfitting, and vice versa for underfitting. Accuracy of the classification can be evaluated using the validation image set by calculating the percentage of correctly classified images. A "Z'" score measuring the accuracy of the network can be calculated from this. Z' scores larger than 0.5 indicate a good screening assay. With pre-trained networks, the number of images for training can be relatively low, preferably with a minimum of about 500 training images.

The classification into WT and disease is an example of supervised learning, because during training the information of whether an image is WT or disease is given to the network. Supervised training strategies are the natural choice when the image classes are known beforehand (WT and disease).

In some embodiments, unsupervised learning is used in accordance with the methods described herein. An example of unsupervised learning includes the use of autoencoders. See FIG. 1. The encoder and decoder neural networks are trained such that the reconstructed data matches the input data as closely as possible, resulting in a low-dimensional representation of the data in the latent space. An autoencoder is a type of artificial neural network used to learn efficient data codings in an unsupervised manner, with the aim of reproducing an input as an output. An autoencoder is typically designed to learn a representation (encoding) for a set of data, typically for dimensionality reduction, by training the network to ignore signal "noise". Along with the reduction side, a reconstructing side is learnt, where the autoencoder tries to generate from the reduced encoding a representation as close as possible to its original input, hence its name.

A typical autoencoder contains an input layer, a hidden layer, and an output layer. Further, input data passes through the input layer and enters the hidden layer. The number of nodes in the hidden layer is typically smaller than the number of nodes in the input layer, a dimension of the data is reduced. Therefore, a compression or encoding is performed. Following encoding, the data output from the hidden layer enters the output layer. Typically, since the number of nodes in the output layer is larger than the number of nodes in the hidden layer, the dimension of the data is increased. Thus, a decompression or decoding is performed.

The unsupervised nature of this machine learning method has the advantage that the autoencoder learns a representation of the data without any additional information about the data (such as that it is derived from wild type or disease cell lines), and is thus unbiased in estimating the toxicity of compounds. The representation of the data in terms of vectors also has the advantage that differences in the wild type and disease phenotype can be removed from the vector space, since this difference is not relevant in determining toxicity. In exemplary embodiments, an autoencoder, particularly a convolutional autoencoder, can be used to determine toxicity by:

(a) removing the distance between wild type and disease from the latent space;
(b) calculating the distance from the mean vector of the wild type phenotypes and disease phenotype;
(c) comparing the distance calculated from step (b) and the standard deviation of the wild type phenotype and disease phenotype; and
(d) determining a toxicity value.

Figure 2A:
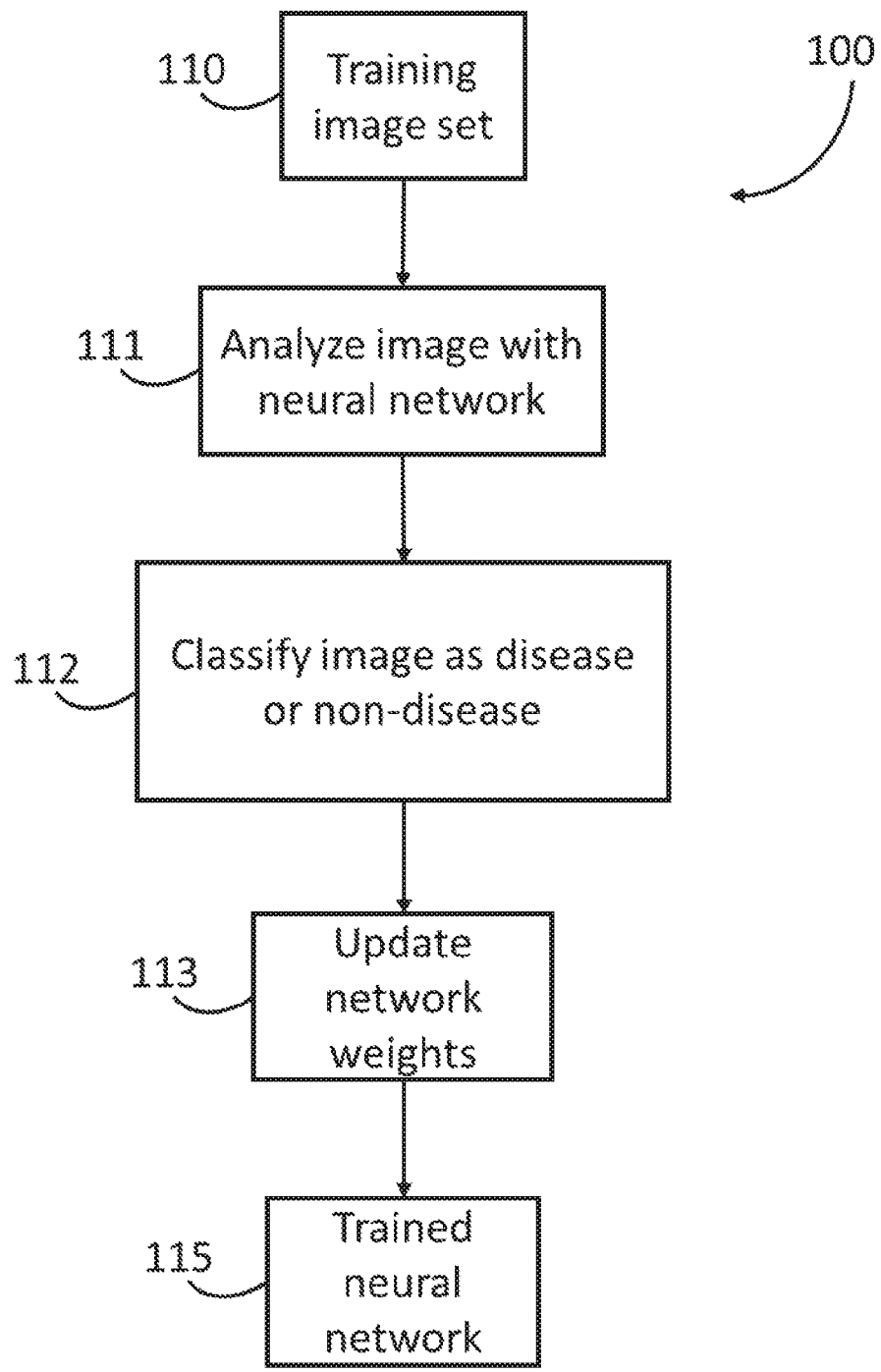

A flow chart showing an exemplary implementation of neural network training in shown in FIG. 2A. Training process 100 begins at block 110 with a training image set. The training image set 110 can contain images from non-disease and disease phenotype organoids as described above. Images are first augmented by applying a set of image transformations (e.g., as described above). At block 111, individual images are analyzed by the neural network, and then classified by the neural network at block 112 as being from a disease or non-disease organoid. The classification is compared to the true value and the network weights are updated in block 113 so that the next time the neural network is shown the image the classification is more likely to be closer to the true value. All images in the training set are shown to the network, the process is then repeated a pre-determined number of times (e.g., about 500 times). Training is complete after all repetitions have been completed, providing a trained neural network at block 115.

5.2.5. Analysis

Once a neural network is "trained" to a satisfactory level it can be used as an analytical tool on other data. To do this, the user no longer specifies any training runs and instead allows the network to work in forward propagation mode only. New inputs are presented to the input pattern where they filter into and are processed by the middle layers as though training were taking place, however, at this point the output is retained and no backpropagation occurs. The output of a forward propagation run is the predicted model for the data which can then be used for further analysis and interpretation.

The neural networks of the disclosure can be used to analyze images from organoids exposed to test molecules. Images from organoids treated with test molecules can be analyzed by the network, which can assign a probability score between 0 and 1 (or 0% to 100%, 0 to 10 or any arbitrary range) to each image, where 1 represents WT and 0 represents disease. Scores can be averaged for different organoids treated with the same compound (e.g., to give a score for the compound). The score gives an indication of how much the disease phenotype has been reverted to WT. Compounds can be ranked by their score, with compounds scoring >0.95 identified as very clearly reverting the disease phenotype to WT.

The accuracy of the network is preferably verified by using untreated control organoids. Untreated control organoids, preferably both non-disease and disease organoids, can be classified as disease or non-disease similar to treated organoids, and the neural network can be deemed to be accurate if the control organoids are correctly classified more than a cutoff amount. For example, the neural network can be deemed to be accurate if the control organoids are correctly classified as non-disease or disease more than 50%, more than 60%, more than 70%, more than 80%, more than 90%, or more than 95% of the time. In some embodiments, accuracy verification is performed simultaneously with compound screening.

Figure 2B:
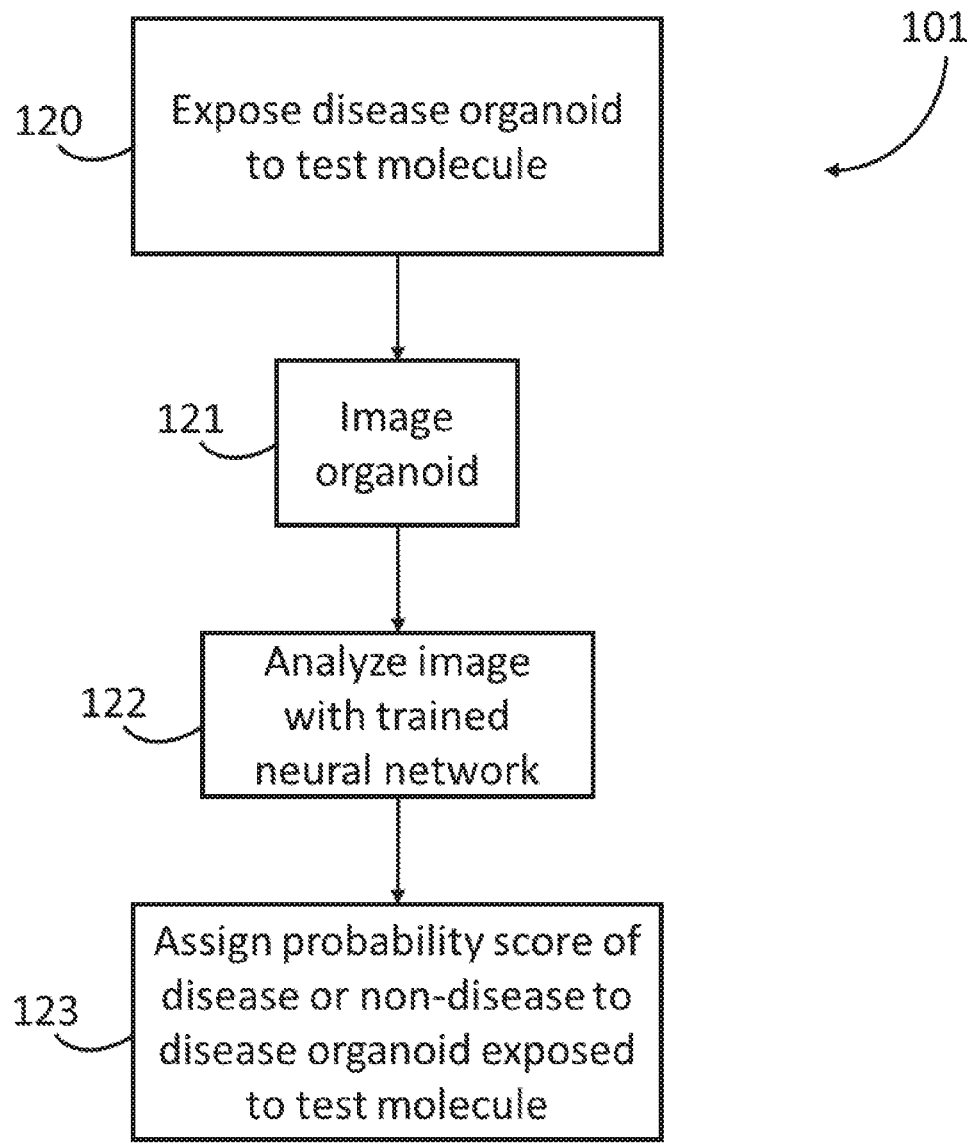

A flow chart showing an exemplary implementation of a process for identifying biologically active molecules against a disease is shown in FIG. 2B. Process 101 begins at block 120, where a disease organoid is exposed to a test molecule (e.g., as described in Section 5.3.3). The organoid is then imaged at block 121 to obtain one or more images of the organoid. The image(s) are then analyzed by a trained neural network that has been trained to assign a probability score of disease or non-disease at block 122. Finally, the neural network assigns a probability score of disease or non-disease to the disease organoid exposed to the test molecule at block 123. The test molecule can be identified as biologically active against the disease if the probability score indicates a reversion of the disease phenotype to the non-disease phenotype (e.g., as determined by comparing the probability score to a cutoff as described in Section 5.3.3).

5.2.6. Toxicity

Toxicity can also be analyzed using the same classification network as described above, but by using the neurons (e.g., 512 neurons as described in Section 5.2.1) of a fully connected layer upstream of the last two neurons. In a preferred embodiment, a penultimate fully connected layer is used. A fully connected upstream layer of 512 neurons can be seen as a 512-dimensional vector that contains more information than the final 2-dimensional (non-disease vs disease) vector. The information contained in this high-dimensional latent vector can be used to define a measure of how toxic a compound is. In some embodiments, an autoencoder (e.g., a convolutional autoencoder or other autoencoder such as a variational, sparse, or denoising autoencoder) is used in analyzing toxicity.

Each organoid image that is analyzed by the network gives a latent vector in addition to a phenotype (WT vs disease) score. Latent vectors for organoids exposed to the same compound can be averaged, as can WT and disease latent vectors. These vectors can optionally be clustered by using t-distributed stochastic neighbor embedding (t-SNE) into a two-dimensional space. Other dimensionality-reducing methods like principal component analysis (PCA) can also be used. The distance of a latent vector of organoids treated with a test molecule to the nearest untreated organoid vector (WT or disease) can be defined as the toxicity of the compound, because it gives a measure of how far away from either WT or disease the treated organoids are. In a preferred embodiment, the upstream latent vector is clustered prior to determining the distances. This distance can be normalized to be between 0 and 1 (or 0 to 10, 0% to 100% or any arbitrary range) to span an axis additional to the WT-disease axis. The difference between WT and disease can be considered less relevant for more toxic test compounds. Accordingly, the WT-disease axis can be compressed linearly for increasing toxicity, which results in each compound located within an equilateral triangle, the corners of which signify compounds that have a WT, disease or toxic phenotype, respectively. This is illustrated in FIG. 13.

In one embodiment, toxicity is determined by first (a) extracting a fully connected layer upstream of the two last nodes; and (b) quantifying a difference between the first mammalian cell population that has contacted a test molecule, latent vector associated with the first cell population that has not contacted a test molecule, and the latent vector associated with the second cell population, to provide a degree of difference with the first mammalian cell population that has contacted a test molecule, latent vector associated with the first cell population that has not contacted a test molecule, and the latent vector associated with the second cell population.

The degree of difference is calculated by taking the minimum of the difference between the latent vector associated with the first mammalian cell population that has contacted a test molecule, latent vector associated with the first cell population that has not contacted a test molecule, and the latent vector associated with the second cell population.

The degree of difference can be determined across an entire latent space. In one embodiment, the latent space comprises at least 10, at least 100, at least 250, at least 400, at least 500, at least 600, at least 800, or at least 1000 dimensions.

Figure 2C:
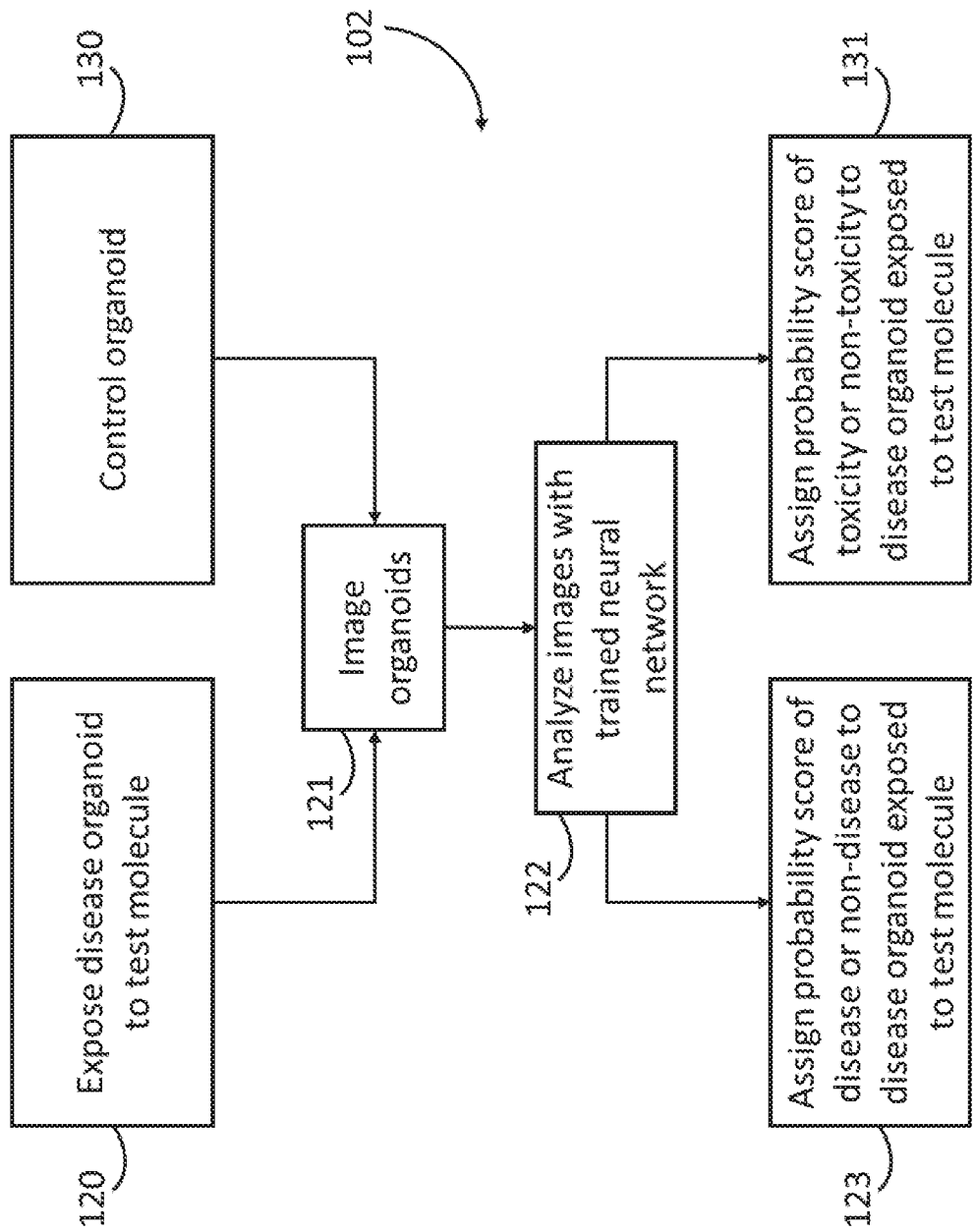

A flow chart showing an exemplary implementation of a process for identifying biologically active molecules against a disease and evaluating toxicity is shown in FIG. 2C. In process 102, blocks 120, 121, 122, and 123 correspond to blocks 120, 121, 122, and 123 of process 101 as shown in FIG. 2B. Process 102 further includes culturing one or more control organoids at block 130, which are organoids not exposed to the test molecule and which preferably include non-disease organoids and disease organoids. The control organoids are imaged at block 121 and analyzed with the trained neural network at block 122. At block 131, the trained neural network assigns a probability score of toxicity or non-toxicity to the disease organoid exposed to the test molecule. It some instances, it may be desirable to perform process 102 with block 123 omitted, for example, when evaluating toxicity of test molecules previously identified as biologically active.

In one embodiment, the toxicity can be defined on a scale between 0 (no toxicity) and 1 (largest toxicity, i.e. the non-disease organoid that has contacted a test molecule which is furthest away from the non-disease organoid in the latent space) by normalizing the distances in the latent space by the largest occurring distance.

5.2.7. Dose Response Analysis

The systems and methods of the disclosure may further include optional dose response analysis features such as $IC_{50}$ and $LC_{50}$. The following four-parameter logistic function can be used to fit to the dose response:

$$y=\min+(\max-\min)/(1+10\textasciicircum((x-\log(IC50))*\text{slope}))$$

where x is the logarithm of the test molecule concentration, and y is the therapeutic potential. The parameter $IC_{50}$ is the required value. The same function can be used for $LC_{50}$. The four parameters of the equation can be fit to the data using a nonlinear least-square fit (e.g., using the Levenberg-Marquardt algorithm or Trust Region Reflective algorithm). The open source Python package script or any other software with curve fitting can be used, e.g., Matlab, R, or Excel.

5.2.8. Computing Requirements

Network training and analysis can be carried out on any computer, but is preferably performed on graphical processing units (GPUs) since computations performed during training can be done in optimal ways on GPUs (e.g., they can speed up the training process significantly). Training with thousands of images can done in less than an hour with a modern computer (e.g., 12 cores, 64 GB RAM) equipped with a GPU, e.g. an NVIDIA GeForce 1080 Ti. The training time can be reduced with more computational power, e.g. a computer with multiple graphics cards used in parallel.

5.3. Applications of the Neural Networks of the Disclosure

The systems and methods of the disclosure can be used to identify and interpret disease phenotypes and their reversal that are hidden behind a large biological variability. Deep neural networks as described herein are ideally suited for this challenge, since they can identify and combine multiple features that differ between WT and disease organoids in an optimal, unbiased way.

Single or multiple microscopy images of each organoid can be acquired, with multiple images of each organoid being preferred. The images can be either 2D or 3D. Each image of an organoid is referred to herein as a "channel." Multiple channels can be obtained, for example, by using different filters (e.g., 3-4 filters). Information about structure and different protein expression (e.g., differentiation markers, DAPI, membrane stain, mitochondrial markers, etc.), can be combined to obtain a unique fingerprint of the WT and a disease phenotype. The fingerprint can include numbers of cells/area of the signal, intensity, shape, etc. Single cells and cell layers can also be used in the methods of the disclosure instead of organoids, however, organoids are preferred because organoids made using micropatterns can be more reproducible than single cells or cell layers.

In one embodiment, an organoid is stained with 1, 2, 3, 4, or 5 different stains, each stain having a distinct color.

The neural networks of the disclosure can be used to learn the differences between WT and disease cells, cell layers, and organoids during training. The trained networks of the disclosure can then be shown images of organoids treated by test molecules, and classify the images as to how much they resemble the WT on a score from 0 to 1 (or 0 to 10 or 0% to 100% or any arbitrary range). Images with a score close to 1 can be defined as hits that have successfully rescued the phenotype. The potential toxicity of hit compounds can also be analyzed simultaneously.

The neural networks and methods of the disclosure are not only useful for testing drugs, but can also be used to test the effectiveness of genetic manipulations for phenotypic reversal. For example, an allele carrying a mutation that causes a disease may be silenced, or, if an affected gene causes a loss of function, the wild type gene could be overexpressed to attempt to compensate. As illustrated in the Examples, this strategy has been shown to work in the case of Huntington's disease, where the wild type Huntingtin gene was overexpressed on the background of a cell line carrying a Huntingtin knockout (KO). The derived organoids can be tested for phenotypic reversal with the methods described herein. There is not necessarily a need for adding a toxic phenotype when testing such organoids, so the modified organoids can in some embodiments be scored for the probability to be wild type without assessing toxicity.

Advantageously, various embodiments of the systems and methods of the present disclosure utilize a hierarchical analytics framework that can identify and quantify biological properties/analytes from imaging data and then identify and characterize one or more pathologies based on the quantified biological properties/analytes. This hierarchical approach of using imaging to examine underlying biology as an intermediary to assessing pathology provides many analytic and processing advantages over systems and methods that are configured to directly determine and characterize pathology from underlying imaging data.

5.3.1. Organoid Formation

Organoids contain more than one cell type. Organoids typically begin from one cell or a small aggregate that does not display any spatial organization. With time, self-organization occurs and different cell types develop and which dynamically take their correct position within the organoid. The specific spatial organization can differ from one organoid type to another, but differentiation patterns or domains are always present.

In various embodiments, organoids comprise about, no more than, or at least, $10^{12}$ cells, $10^{11}$ cells, $10^{10}$ cells, $10^9$ cells, $10^8$ cells, $10^7$ cells, $10^6$ cells, $10^5$ cells, $10^4$ cells, $10^3$ cells, $10^2$ cells, 10 cells, or a number of cells ranging between any of the foregoing values (e.g., $10^3$ to $10^8$ cells or $10^4$ cells to $10^{10}$ cells or $10^2$ to $10^6$ cells.

In certain aspects of the disclosure, organoids are generated from primary culture cells.

In other aspects, organoids are generated from immortalized cells in culture.

The primary culture cells and the immortalized cells can be stem cells, e.g., totipotent stem cells or pluripotent stem cells.

For example, the following cells can be used, pluripotent cells, induced pluripotent cells, adult stem cells, non-embryonic cells, or non-embryonic stem cells.

In some embodiments the stem cells are human embryonic stem cells. In some embodiments, the cells may be non-embryonic cells, or non-embryonic stem cells. In other embodiments, the stem cells are adult stem cells. In some embodiments, the stem cells are induced pluripotent stem cells. Preferably, the stem cells are of human origin.

In certain specific embodiments, said organoids comprise stem cells or progenitor cells. In specific embodiments, said stem cells or progenitor cells are embryonic stem cells, embryonic germ cells, induced pluripotent stem cells, mesenchymal stem cells, bone marrow-derived mesenchymal stem cells, bone marrow-derived mesenchymal stromal cells, umbilical cord stem cells, amniotic fluid stem cells, amnion derived adherent cells (AMDACs), osteogenic placental adherent cells (OPACs), adipose stem cells, limbal stem cells, dental pulp stem cells, myoblasts, endothelial progenitor cells, neuronal stem cells, exfoliated teeth derived stem cells, hair follicle stem cells, dermal stem cells, parthenogenically derived stem cells, reprogrammed stem cells, amnion derived adherent cells, or side population stem cells. In certain other specific embodiments, said organoids comprise hematopoietic stem cells or hematopoietic progenitor cells.

In certain other specific embodiments, any of the organoids described herein comprise differentiated cells. In more specific embodiments, said differentiated cells comprise one or more of:

endothelial cells, epithelial cells, dermal cells, endodermal cells, mesodermal cells, fibroblasts, osteocytes, chondrocytes, natural killer cells, dendritic cells, hepatic cells, pancreatic cells, or stromal cells;

salivary gland mucous cells, salivary gland serous cells, von Ebner's gland cells, mammary gland cells, lacrimal gland cells, ceruminous gland cells, eccrine sweat gland dark cells, eccrine sweat gland clear cells, apocrine sweat gland cells, gland of Moll cells, sebaceous gland cells. bowman's gland cells, Brunner's gland cells, seminal vesicle cells, prostate gland cells, bulbourethral gland cells, Bartholin's gland cells, gland of Littre cells, uterus endometrium cells, isolated goblet cells, stomach lining mucous cells, gastric gland zymogenic cells, gastric gland oxyntic cells, pancreatic acinar cells, paneth cells, type II pneumocytes, clara cells, somatotropes, lactotropes, thyrotropes, gonadotropes, corticotropes, intermediate pituitary cells, magnocellular neurosecretory cells, gut cells, respiratory tract cells, thyroid epithelial cells, parafollicular cells, parathyroid gland cells, parathyroid chief cell, oxyphil cell, adrenal gland cells, chromaffin cells, Leydig cells, theca interna cells, corpus luteum cells, granulosa lutein cells, theca lutein cells, juxtaglomerular cell, macula densa cells, peripolar cells, mesangial cell, blood vessel and lymphatic vascular endothelial fenestrated cells, blood vessel and lymphatic vascular endothelial continuous cells, blood vessel and lymphatic vascular endothelial splenic cells, synovial cells, serosal cell (lining peritoneal, pleural, and pericardial cavities), squamous cells, columnar cells, dark cells, vestibular membrane cell (lining endolymphatic space of ear), stria vascularis basal cells, stria vascularis marginal cell (lining endolymphatic space of ear), cells of Claudius, cells of Boettcher, choroid plexus cells, pia-arachnoid squamous cells, pigmented ciliary epithelium cells, nonpigmented ciliary epithelium cells, corneal endothelial cells, peg cells, respiratory tract ciliated cells, oviduct ciliated cell, uterine endometrial ciliated cells, rete testis ciliated cells, ductulus efferens ciliated cells, ciliated ependymal cells, epidermal keratinocytes, epidermal basal cells, keratinocyte of fingernails and toenails, nail bed basal cells, medullary hair shaft cells, cortical hair shaft cells, cuticular hair shaft cells, cuticular hair root sheath cells, hair root sheath cells of Huxley's layer, hair root sheath cells of Henle's layer, external hair root sheath cells, hair matrix cells, surface epithelial cells of stratified squamous epithelium, basal cell of epithelia, urinary epithelium cells, auditory inner hair cells of organ of Corti, auditory outer hair cells of organ of Corti, basal cells of olfactory epithelium, cold-sensitive primary sensory neurons, heat-sensitive primary sensory neurons, Merkel cells of epidermis, olfactory receptor neurons, pain-sensitive primary sensory neurons, photoreceptor rod cells, photoreceptor blue-sensitive cone cells, photoreceptor green-sensitive cone cells, photoreceptor red-sensitive cone cells, proprioceptive primary sensory neurons, touch-sensitive primary sensory neurons, type I carotid body cells, type II carotid body cell (blood pH sensor), type I hair cell of vestibular apparatus of ear (acceleration and gravity), type II hair cells of vestibular apparatus of ear, type I taste bud cells, cholinergic neural cells, adrenergic neural cells, peptidergic neural cells, inner pillar cells of organ of Corti, outer pillar cells of organ of Corti, inner phalangeal cells of organ of Corti, outer phalangeal cells of organ of Corti, border cells of organ of Corti, Hensen cells of organ of Corti, vestibular apparatus supporting cells, taste bud supporting cells, olfactory epithelium supporting cells, Schwann cells, satellite cells, enteric glial cells, astrocytes, neurons, oligodendrocytes, spindle neurons, anterior lens epithelial cells, crystallin-containing lens fiber cells, hepatocytes, adipocytes, white fat cells, brown fat cells, liver lipocytes, kidney glomerulus parietal cells, kidney glomerulus podocytes, kidney proximal tubule brush border cells, loop of Henle thin segment cells, kidney distal tubule cells, kidney collecting duct cells, type I pneumocytes, pancreatic duct cells, nonstriated duct cells, duct cells, intestinal brush border cells, exocrine gland striated duct cells, gall bladder epithelial cells, ductulus efferens nonciliated cells, epididymal principal cells, epididymal basal cells, ameloblast epithelial cells, planum semilunatum epithelial cells, organ of Corti interdental epithelial cells, loose connective tissue fibroblasts, corneal keratocytes, tendon fibroblasts, bone marrow reticular tissue fibroblasts, nonepithelial fibroblasts, pericytes, nucleus pulposus cells, cementoblast/cementocytes, odontoblasts, odontocytes, hyaline cartilage chondrocytes, fibrocartilage chondrocytes, elastic cartilage chondrocytes, osteoblasts, osteocytes, osteoclasts, osteoprogenitor cells, hyalocytes, stellate cells (ear), hepatic stellate cells (Ito cells), pancreatic stelle cells, red skeletal muscle cells, white skeletal muscle cells, intermediate skeletal muscle cells, nuclear bag cells of muscle spindle, nuclear chain cells of muscle spindle, satellite cells, ordinary heart muscle cells, nodal heart muscle cells, Purkinje fiber cells, smooth muscle cells, myoepithelial cells of iris, myoepithelial cell of exocrine glands, reticulocytes, megakaryocytes, monocytes, connective tissue macrophages. epidermal Langerhans cells, dendritic cells, microglial cells, neutrophils, eosinophils, basophils, mast cell, helper T cells, suppressor T cells, cytotoxic T cell, natural Killer T cells, B cells, natural killer cells, melanocytes, retinal pigmented epithelial cells, or oogonia/oocytes, spermatids, spermatocytes, spermatogonium cells, spermatozoa, ovarian follicle cells, Sertoli cells, thymus epithelial cell, and/or interstitial kidney cells.

In certain specific embodiments of any of the organoids presented herein, said organoids perform at least one function of a liver, kidney, pancreas, thyroid lung, intestine, colon, prostate, brain, breast, ovary, stomach, esophagus, lingual tissue, taste bud, inner ear, or retina.

Appropriate culture conditions for mammalian cells are well known in the art or can be determined by the skilled artisan (see, for example, Animal Cell Culture: A Practical Approach $2^{nd}$ Ed., Rickwood, D. and Hames, B. D., eds. (Oxford University Press: New York, 1992)), and vary according to the particular cell selected. Commercially available media can be utilized. Non-limiting examples of media include, for example, Dulbecco's Modified Eagle Medium (DMEM, Life Technologies), Dulbecco's Modified Eagle Medium/Nutrient Mixture F-12 (DMEM/F-12, Life Technologies), Minimal Essential Medium (MEM, Sigma, St. Louis, Mo.), and hepatocyte medium.

The media described above can be supplemented as necessary with supplementary components or ingredients, including optional components, in appropriate concentrations or amounts, as necessary or desired. Cell medium solutions provide at least one component from one or more of the following categories: (1) an energy source, usually in the form of a carbohydrate such as glucose; (2) all essential amino acids, and usually the basic set of twenty amino acids plus cysteine; (3) vitamins and/or other organic compounds required at low concentrations; (4) free fatty acids or lipids, obtained from purified gelatin, plant material, or animal byproducts; (4) nucleosides and bases such as, adenosine, thymidine, and hypoxanthine; (5) buffers, such as HEPES; (6) antibiotics, such as gentamycin or ampicillin; (7) cell protective agents, for example, pluronic polyol; and (8) galactose.

The culture can be supplemented with reagents to promote organoid formation. Exemplary reagents that have been used in the art to promote organoid formation include EGF, FGF10, HGF, R-spondin, BMP4, WNT3A, retinoic acid, GSK3β inhibitors, TGF-β inhibitors, HDAC inhibitors, ROCK inhibitors, Noggin, Activin A, p38 inhibitors and Gastrin. Table 1 below shows reagents that can be used to promote formation of different types of organoids.

TABLE 1

| Organoid type | Reagents | Reference |
|---|---|---|
| Stomach | ROCK inhibitor (Y-27632), Activin A, BMP5, WNT, FGF, Noggin, Retinoic acid, EGF | McCracken et al., 2014, Nature 516(7531): 400-4 |
| Stomach | EGF, R-spondin, Noggin, FGF10, WNT, Gastrin, Nicotinamide, TGFβ inhibitor | Bartfeld et al., 2015, Gastroenterology 148(1): 126-136 |
| Intestine | Activin A, BMP4, FGF4, WNT3A, R-Spondin1, Noggin, EGF, WNT | Spence et al., 2011, Nature 470(7332): 105-9 |
| Intestine | EGF, R-spondin, Noggin, WNT3A, Nicotinamide, Gastrin, TGFβ inhibitor, p38 inhibitor | Sato et al., 2011, Gastroenterology 141(5): 1762-72 |
| Colon | EGF, R-spondin, Noggin, WNT3A, Nicotinamide, Gastrin, TGF-β inhibitor, p38 inhibitor | Sato et al., 2011, Gastroenterology 141(5): 1762-72 |
| Liver | Noggin, WNT, ROCK inhibitor, Gastrin, EGF, R-spondin, FGF10, hepatocyte growth factor, nicotinamide, TGF-β inhibitor, Forskolin | Huch et al., 2015, Cell 160(1-2): 299-312 |
| Liver | Activin A, BMP4, FGF2, hepatocyte growth factor, Oncostatin M | Si-Tayeb et al., 2010, Hepatology 51(1): 297-305 |
| Pancreas | TGF-β inhibitors, Noggin, R-Spondin 1, WNT3A, EGF, FGF10, Nicotinamide | Boj et al., 2015, Cell 160(1-2): 324-38 |
| Prostate | EGF, R-Spondin 1, Noggin, TGF-β inhibitor, p38 MAP kinase inhibitor, FGF10, FGF2, PGE2, Nicotinamide, DHT | Karthaus et al., 2014, Cell 159(1): 163-175 |
| Lung | Activin A; BMP, TGF-β and Wnt inhibitors; Wnt, BMP, FGF, RA activators; Wnt, FGF, cAMP and glucocorticoids | Dye et al., 2015, eLife. 4: e05098 |
| Brain | N2 supplement, NEAA and heparin 2-mercaptoethanol, insulin, Vitamin A, retinoic acid | Lancaster et al., 2013, Nature 501(7467): 373-9 |
| Kidney | Wnt, GSK3α inhibitor, FGF9 | Takasato et al., 2015, Nature 526(7574): 564-8; Takasato et al., 2016, Nat. Protoc. 11(9): 1681-92 |
| Cardiomyocytes | Activin A | Lundy et al., 2013, Stem Cells and Dev., 22(14): 1991-2002 | for example linoleic acid; and (5) trace elements, where trace elements are defined as inorganic compounds or naturally occurring elements that are typically required at very low concentrations, usually in the micromolar range.

The medium also can be supplemented electively with one or more components from any of the following categories: (1) salts, for example, magnesium, calcium, and phosphate; (2) hormones and other growth factors such as, serum, insulin, transferrin, epidermal growth factor and fibroblast growth factor; (3) protein and tissue hydrolysates, for example peptone or peptone mixtures which can be Cells maintained in culture can be passaged by their transfer from a previous culture to a culture with fresh medium. In one embodiment, organoid-producing cells (e.g., human embryonic stem cells, iPSC from human epithelial cells) are stably maintained in cell culture for at least 3 passages, at least 4 passages, at least 5 passages, at least 6 passages, at least 7 passages, at least 8 passages, at least 9 passages, at least 10 passages, at least 11 passages, at least 12 passages, at least 13 passages, at least 14 passages, at least 15 passages, at least 20 passages, at least 25 passages, or at least 30 passages.

The organoid-producing cells can harbor introduced expression vectors (constructs), such as plasmids and the like. The expression vector constructs can be introduced via transformation, microinjection, transfection, lipofection, electroporation, or infection. The expression vectors can contain coding sequences, or portions thereof, encoding the proteins for expression and production. Expression vectors containing sequences encoding the produced proteins and polypeptides, as well as the appropriate transcriptional and translational control elements, can be generated using methods well known to and practiced by those skilled in the art. These methods include synthetic techniques, in vitro recombinant DNA techniques, and in vivo genetic recombination which are described in J. Sambrook et al., 1989, Molecular Cloning, A Laboratory Manual, Cold Spring Harbor Press, Plainview, N.Y. and in F. M. Ausubel et al., 1989, Current Protocols in Molecular Biology, John Wiley & Sons, New York, N.Y.

In some embodiments, the organoid-producing cells are cultured in a microwell plate (e.g., a 24 or 96 well plate), preferably under conditions that produce 20 to 30 organoids per well.

In an embodiment, the organoid-producing cells are plated into wells of a 24 well plate at a final density of 75,000 cells per well. In another embodiment, the cells are plated into wells of a 24 well plate at a final density of about 50,000 cells per well, about 55,000 cells per well, about 60,000 cells per well, about 65,000 cells per well, about 70,000 cells per well, about 75,000 cells per well, about 80,000 cells per well, about 85,000 cells per well, about 90,000 cells per well, about 95,000 cells per well, or about 100,000 cells per well.

In another embodiment, cells are plated into wells of a 24 well plate at a final density of at least 50,000 cells per well, at least 55,000 cells per well, at least 60,000 cells per well, at least 65,000 cells per well, at least 70,000 cells per well, at least 75,000 cells per well, at least 80,000 cells per well, at least 85,000 cells per well, at least 90,000 cells per well, at least 95,000 cells per well, or at least 100,000 cells per well.

In one embodiment, a total change of media occurs every 3 days. In one embodiment, a total change of media occurs every 4 days. In another embodiment, a total change of media occurs at least every day, at least every 2 days, at least every 3 days, at least every 4 days, at least every 5 days, at least every 6 days, at least every 7 days, at least every 8 days, at least every 9 days, at least every 10 days, at least every 11 days, at least every 12 days, at least every 13 days, or at least every 14 days.

Various types of stem cells can be used to make organoids. For example, human pluripotent stem cells (hPSCs), such as induced pluripotent stem cells (iPSCs) (see, e.g., McCracken et al., 2014, Nature 516(7531):400-4; Spence et al., 2011, Nature 470(7332):105-9; Si-Tayeb et al., 2010, Hepatology 51(1):297-305; Dye et al., 2015, eLife. 4: e05098; Lancaster et al., 2013, Nature 501(7467):373; Takasato et al., 2015, Nature 526(7574):564-8; Takasato et al., 2016, Nat. Protoc. 11(9):1681-92) and human adipose derived stem cells (hAdSCs) (see, e.g., Bartfeld et al., 2015, Gastroenterology 148(1):126-136; Sato et al., 2011, Gastroenterology 141(5): 1762-72; Huch et al., 2015, Cell 160(1-2):299-312; Boj et al., 2015, Cell 160(1-2):324-38; Karthaus et al., 2014, Cell 159(1):163-175) can be used. Human embryonic stem cell lines, such as RUES-1 or RUES-2 (rues.rockefeller.edu) can also be used.

The composition of the solution of extracellular matrix components will vary according to the tissue produced. Representative extracellular matrix components include, but are not limited to, collagen, laminin, fibronectin, vitronectin, elastin, glycosaminoglycans, proteoglycans, and combinations of some or all of these components (e.g., Matrigel™, Collaborative Research, Catalog No. 40234). In tissues containing cell types which are responsive to mechanical forces, the solution of extracellular matrix components preferably gels or coalesces such that the cells are exposed to forces associated with the internal tension in the gel.

Organoid formation can be promoted by spatially confining stem cells during differentiation. Stem cells can be seeded on surfaces with micropatterned extracellular matrix proteins, such as laminin, to control the geometry of cell colonies. Both the size of the micropattern and the type of medium affect the differentiation patterning outcome (see, e.g., Deglincerti et al. 2016, Nature Protocols 11: 2223-2232; Deglincerti et al. 2016, Current Topics in Developmental Biology, (116):99-113; Metzger et al., 2018, Current Opinion in Genetics & Development, 52:86-91; Etoc et al., 2016, Developmental Cell, 39(3):302-315). Differentiation of stem cells on micropatterns allows for different tissue types to be generated in a reproducible manner. 3D scaffolds, for example made using a hydrogel such as Matrigel™, can also be used (see, e.g., Yin et al., 2016, Cell Stem Cell, 18(1):25-28).

In other embodiments, organoids are produced in vitro from the individual cells of a tissue of interest, for example according to the exemplary process described below.

As a first step in this process, disaggregated or partially disaggregated cells are mixed with a solution of extracellular matrix components to create a suspension. This suspension is then placed in a vessel having a three dimensional geometry which approximates the in vivo gross morphology of the tissue and includes tissue attachment surfaces coupled to the vessel. The cells and extracellular matrix components are then allowed to coalesce or gel within the vessel, and the vessel is placed within a culture chamber and surrounded with media under conditions in which the cells are allowed to form an organized tissue connected to the attachment surfaces.

Although this method is compatible with the in vitro production of a wide variety of tissues, it is particularly suitable for tissues in which at least a subset of the individual cells are exposed to and impacted by mechanical forces during tissue development, remodeling or normal physiologic function. Examples of such tissues include muscle, bone, skin, nerve, tendon, cartilage, connective tissue, endothelial tissue, epithelial tissue, and lung. More specific examples include skeletal and cardiac (i.e., striated), and smooth muscle, stratified or lamellar bone, and hyaline cartilage. Where the tissue includes a plurality of cell types, the different types of cells may be obtained from the same or different organisms, the same or different donors, and the same or different tissues. Moreover, the cells may be primary cells or immortalized cells. Furthermore, all or some of the cells of the tissue may contain a foreign DNA sequence (for example a foreign DNA sequence encoding a receptor) which indicates the response to a bioactive compound (as described herein).

The composition of the solution of extracellular matrix components will vary according to the tissue produced. Representative extracellular matrix components include, but are not limited to, collagen, laminin, fibronectin, vitronectin, elastin, glycosaminoglycans, proteoglycans, and combinations of some or all of these components (e.g., Matrigel™, Collaborative Research, Catalog No. 40234). In tissues containing cell types which are responsive to mechanical forces, the solution of extracellular matrix components preferably gels or coalesces such that the cells are exposed to forces associated with the internal tension in the gel.

An apparatus for producing a tissue in vitro having an in vivo-like gross and cellular morphology includes a vessel having a three dimensional geometry which approximates the in vivo gross morphology of the tissue. The apparatus also includes tissue attachment surfaces coupled to the vessel. Such a vessel may be constructed from a variety of materials which are compatible with the culturing of cells and tissues (e.g., capable of being sterilized and compatible with a particular solution of extracellular matrix components) and which are formable into three dimensional shapes approximating the in vivo gross morphology of a tissue of interest. The tissue attachment surfaces (e.g., stainless steel mesh, Velcro™, or the like) are coupled to the vessel and positioned such that as the tissue forms in vitro the cells may adhere to and align between the attachment surfaces. The tissue attachment surfaces may be constructed from a variety of materials which are compatible with the culturing of cells and tissues (e.g., capable of being sterilized, or having an appropriate surface charge, texture, or coating for cell adherence).

The tissue attachment surfaces may be coupled in a variety of ways to an interior or exterior surface of the vessel. Alternatively, the tissue attachment surfaces may be coupled to the culture chamber such that they are positioned adjacent to the vessel and accessible by the cells during tissue formation. In addition to serving as points of adherence, in certain tissue types (e.g., muscle), the attachment surfaces allow for the development of tension by the tissue between opposing attachment surfaces.

5.3.2. Organoids with Disease Phenotypes

The methods of the disclosure entail identifying molecules that revert a disease phenotype in an organoid. In some embodiments, the disease phenotype is associated with a CNS disorder. For example, the disease phenotype can be associated with a neurodegenerative disorder (e.g., Huntington's disease, Alzheimer's disease, Parkinson's disease, Rett syndrome, or ALS), autism spectrum disorder, or a psychiatric disease (e.g., schizophrenia, bipolar disorder, epilepsy). In other embodiments, the disease phenotype is associated with a cancer. In yet other embodiments, the disease phenotype is associated with an infectious disease. In yet other embodiments, the disease phenotype is associated with CF.

Disease phenotypes in organoids can be created, for example, by genetically modifying a normal stem cell line to contain a genetic defect associated with a disease phenotype of interest (e.g., using CRISPR-Cas9 or TALEN). Thus, in some embodiments, organoids having a disease phenotype contain one or more mutations that confer the disease phenotype compared to a normal cell line. In a specific embodiment, the organoid having a disease phenotype encodes a Huntingtin protein with an expanded polyglutamine ("poly Q") repeat. See, e.g., WO/2017/147536. The poly Q repeat can be, for example, 42-150 glutamine residues (e.g., 42, 45, 58, 50, 56, 58, 67, 72, 74, or 150 glutamine residues).

Organoids having a disease phenotype can also be generated from iPSCs from subjects have the disease, by using a chemical inducer, by viral infection, or by expression of a transgene. See, e.g., Clevers, 2018, Cell 165:1586-1597; Ho et al., 2018, Int J Mol Sci. 19(4):936; Dutta et al., 2017, Trends Mol Med. 23(5):393-410.

Cells having the same or closely similar genotypes can be considered "isogenic." For example, a normal stem cell can be modified to have a disease form of a gene, and the resulting modified cell line can be considered isogenic to the normal cell line. As another example, a stem cell line having a mutant gene associated with a disease phenotype can be corrected to provide a stem cell line having a non-disease phenotype that is isogenic to the parental stem cell line. Other variations may include the incorporation of one, two three or more markers, and/or one or more variations unintentionally introduced when modifying the parental cell line (e.g., an off-target mutation introduced when using CRISPR-Cas9 mediated gene editing). The resulting cell will still be considered isogenic to the cell from which it was modified. In some of the methods described herein, an isogenic control cell or an isogenic wild-type cell is used. Cell line pairs (and organoids made from such cell line pairs) that are isogenic, e.g., they share the same genetic background except for one or a small number (such as 2, 3, 4, 5, or 10) of variances (for example variances that are introduced by genetically modifying the cell), allow for the study of specific genetic variances compared to the wild-type cells and alleviate complications introduced by comparing different patient cells which can vary by a multitude of genetic features (especially but not exclusively genetic features that are not known).

Table 2 shows different types of organoids that have been made in the art and which can be used in the methods of the disclosure (see, e.g., the review article Dutta et al., 2017, Trends Mol Med. 23(5):393-410 and references cited therein).

TABLE 2

| Tissue | Type of Stem Cell | Disease model |
| --- | --- | --- |
| Intestine | human/mouse ASCs | Cancer |
|  | human/mouse ESCs | CF |
|  | human iPSCs | Infectious diseases |
| Colon | human/mouse ASCs | Cancer |
|  |  | Ulcerative colitis |
|  |  | Crohn's disease |
| Liver | human/mouse ASCs | Alagille syndrome |
|  | human iPSCs | CF |
|  |  | Cancer |
|  |  | Lethal liver failure |
| Prostate | mouse/human ASCs | Cancer |
| Lung | human ASCs | Cancer |
|  | mouse fetal cells |  |
| Brain | human ESCs/iPSCs | Autism |
|  | mouse ESCs | Microcephaly |
|  |  | Infectious diseases |
|  |  | Cancer |
| Kidney | human ESCs/iPSCs | Cancer |
| Pancreas | human/mouse ASCs | Cancer |
|  | human iPSCs | CF |
| Breast | human ASCs | Cancer |
| Ovary | human ASCs |  |
| Stomach | human/mouse ASCs | Infectious diseases |
|  | human iPSCs |  |
|  | mouse ESCs |  |
| Esophagus | human/mouse ASCs | Barrett's esophagus |
| Lingual | mouse ASCs | Cancer |
| Taste bud | mouse ASCs |  |
| Inner ear | mouse ESCs |  |
| Retina | mouse ESCs | retinal degeneration |

5.3.3. Methods of Identifying Molecules with Therapeutic Potential

The neural networks of the disclosure can be used to identify molecules with biological activity against a disease.

In one embodiment, the therapeutic potential is given by the final score of the network after the softmax layer. It ranges from 0 (disease) to 1 (wild type). One is the highest score, it most efficiently reverts the phenotype from disease to wild type.

For example, a molecule that is biologically active against a disease can be identified by culturing a mammalian cell population under organoid formation conditions (e.g., as described in Dutta et al., 2017, Trends Mol Med. 23(5):393-410; Clevers, 2018, Cell 165:1586-1597; or Ho et al., 2018, Int J Mol Sci. 19(4):936) in the presence of a test molecule to obtain a organoid, wherein the mammalian cell population, when cultured under the organoid formation conditions in the absence of the test molecule, results in an organoid with a disease phenotype; imaging the organoid following exposure to the test molecule; analyzing one or more images of the organoid using a neural network that has been trained to assign a probability score of disease or non-disease ranging between 0% and 100%; assigning the organoid a probability score ranging between 0% and 100%; wherein the test molecule is biologically active against the disease if the probability score of the organoid is greater than a cutoff probability score of non-disease or lower than a cutoff probability score of disease. Alternatively, test molecules can be applied after organoid formation, with the imaging performed after a period of exposure to the test molecule. The period of exposure to the test molecule (whether present during organoid formation or after organoid formation) can range from several hours to several days to weeks or months, in particular when the test molecule is applied during the whole duration of the experiment. The concentration of test molecules in the culture medium can range from 10 nM to 100 μM (e.g., 10 nM to 1 μM, 10 nM to 50 μM, 10 nM to 20 μM, 1 μM to 100 μM, 1 μM to 50 μM, 1 μM to 20 μM, 1 μM to 10 μM, 10 μM to 50 μM, 20 μM to 50 μM, or 50 μM to 100 μM).

A cutoff probability score of non-disease can, for example, be a value in the range of 60% to 95%, 70% to 95%, 80% to 95%, 90% to 95%, or 95% to 99% (e.g., the cutoff can be 60%, 65%, 70%, 75%, 80%, 85%, 90%, 95%, 96%, 97%, 98%, or 99%). A cutoff probability score of disease can, for example, be a value in the range of 5% to 40%, 5% to 30%, 5% to 20%, 5% to 10%, or 1% to 5% (e.g., the cutoff can be 40%, 35%, 30%, 25%, 20%, 15%, 10%, 5%, 4%, 3%, 2%, or 1%). Thus, for example, if the probability score of non-disease for a disease organoid exposed to a test molecule is 96% and the cutoff probability score of non-disease is 95%, the test molecule can be considered biologically active against the disease. As another example, if the probability score of disease for a disease organoid exposed to a test molecule is 2% and the cutoff probability score of disease is 5%, the test molecule can be considered biologically active against the disease. As yet another example, if the probability score of non-disease for a disease organoid exposed to a test molecule is 60% and the cutoff probability score of non-disease is 90%, the test molecule can be considered not biologically active against the disease.

Prior to imaging organoids in the methods of the disclosure, organoids can be stained for one or more markers such as organelle markers, cell differentiation markers, cell compartment markers, or combinations thereof. The one or more markers preferably includes one or more markers that highlight the gross morphology of the organoid and/or a specific population of cells contained in the organoid. Exemplary staining reagents include nuclear stains (e.g., DAPI and Hoechst nuclear stains), BrdU, calcein green, membrane dyes such as DiI, DiO, DiD, and DiR, Golgi staining reagents such as fluorescently labeled antibodies to GM130, ER staining reagents such as ER-Tracker™ Green (Cell Signaling Technology), phalloidin, and fluorescently labeled antibodies to N-Cadherin, E-Cadherin, ZO-1, and collagen.

Reagents specific to specific types of organoids or types of differentiated cells can also be used. For example, reagents for staining neurofilaments or nestin (e.g., fluorescently labeled antibodies) can be used to stain brain organoids; PAX6 staining reagents can be used to stain neural populations of cells; and SOX10 staining reagents can be used to stain neural crest cells.

Testing can be performed on a collection of test molecules, for example all or part of a small compound library (e.g., a collection ranging from 100 to 100,000 or more test molecules). Compounds can be screened individually or in pools (e.g., in pools of 5 to 100, 10 to 50, 10 to 20, 50 to 100, 5 to 20, or 5 to 10 compounds). If a hit is identified when screening pools of molecules, the molecules of a pool can then be individually tested to identify the specific hit molecule. Thus, the neural networks and methods of the disclosure are useful for high-throughput screening of test compounds.

5.3.3.1. Validation

A single concentration of a test molecule can be used for initial screening of the molecule (e.g., 10 μM). After being identified as a hit, a test molecule can be re-tested at one or more additional concentrations to validate its activity against the disease phenotype. If a high initial concentration is used, retesting a hit at one or more lower concentrations can help to validate the hit, since a too high $IC_{50}$ might indicate high non-specificity of the test molecule.

Validation can comprise re-testing the molecule identified in an initial screen at one or more different concentrations to prepare a dose response curve. Alternatively, or in addition, validation can comprise testing the molecule in an animal model of the disease.

5.3.3.1.1. Dose Response Curves

Validation can comprise determining the $IC_{50}$ and/or $LC_{50}$ of a test molecule. $IC_{50}$ values for test molecules can be generated using the networks of the disclosure and comparing the test concentrations versus the therapeutic potential as measured by the network, e.g., along the base of a WT-disease-toxicity triangle (e.g., a triangle as shown in FIG. 14). $LC_{50}$ values for test molecules can be generated using the networks of the disclosure and comparing the test concentrations versus the toxicity as measured by the network, e.g., along the vertical axis of a WT-disease-toxicity triangle (e.g., a triangle as shown in FIG. 14).

$IC_{50}$ can be measured by testing three or more different concentrations of the test molecule (e.g., 3 to 10, 5 to 10 or 3 to 5) and analyzing the probability scores of disease or non-disease for different concentrations using a nonlinear least-square fit algorithm. Similarly, $LC_{50}$ can be measured by testing three or more different concentrations of the test molecule (e.g., 3 to 10, 5 to 10 or 3 to 5) and analyzing the probability scores of disease or non-disease for different concentrations using a nonlinear least-square fit algorithm.

5.3.3.1.2. Effective Doses

Generally, test molecules closest to the WT phenotype corner of a WT-disease-toxicity triangle will be selected for further analysis and/or development, with compounds having an $IC_{50}$ of less than 5 μM preferred for further development. $LC_{50}$ values are ideally many times greater than the $IC_{50}$, and in some embodiments a test molecule is selected for further analysis or development when the $LC_{50}$ is greater than the $IC_{50}$, when the $LC_{50}$ is at least 10 times greater than the $IC_{50}$, or when the $LC_{50}$ is at least 100 times greater than the $IC_{50}$. Further development can comprise preparing derivatives to identify a derivative with a lower $IC_{50}$ (e.g., less than 100 nM) and/or higher $LC_{50}$ than the original test molecule.

6. EXAMPLES

6.1. Example 1: HD Model Organoid Production and Characterization

The phenotypic signature of HD in a HD model organoid, a hESC-based self-organized structure that mimics the human embryo at neurulation stages, was characterized.

6.1.1. Materials and Methods

Generation of Human Embryonic Stem Cell Lines for use in HD model organoids.

As stated in the Background section, Huntington's disease (HD) is a dominant autosomal neurodegenerative disease that is caused by a mutation that leads to the expansion of a polyQ repeat at the N-terminus of the Huntingtin protein (HTT). Despite years of scrutiny, current animal models fail to accurately recapitulate the pathophysiology of human HD, possibly due to species-specific differences. This has hindered progress toward finding effective candidate therapies for the disease. In order to provide a human platform as a drug screening and research tool to study the function and malfunction of HTT in healthy and >400 cells, this example describes the use of CRISPR/Cas9 genome editing technology to generate the first isogenic human embryonic stem cell lines of HD (and an isogenic wild-type control).

Described in this example is the application of a reverse editing strategy utilizing CRISPR-Cas9 to introduce a large expansion of the polyQ tract in normal hESCs, thus generating HD lines that are genetically identical to wild-type counterparts (except for the polyQ expansion in the HTT gene) and therefore can be termed isogenic. This approach has the advantage of using human pluripotent cells that are stable and can generate all cell types including those that are compromised in HD. Comparative global transcriptome and unbiased metabolome analysis of these lines revealed previously undetected differences caused solely by insertion of an expanded polyQ tract in a single genomic locus.

1A. Generation of Isogenic Human Embryonic Stem Cell Lines

Briefly, CRISPR-Cas9 technology was used to genetically engineer the RUES2 hESC line that was previously derived. The parent cell line, RUES2 is registered with the NIH (NIHhESC-09-0013) and available from the Rockefeller University and WiCell (lot number WB33127); it is a female (XX) line that has a wild type HTT locus (chromosome 4p16.3) that encodes 22Qs on one allele and 24Qs on the second. The 22Q allele was modified by adding 128Qs, thus generating a 150Q line (RUES2-Q150). The relatively large number of resulting polyQs was selected in order to speed up the appearance of disease phenotypes but a smaller number may be used as long as it is 40Q or more as described herein.

A lineage trace marker mCherry and blastidicine cassette were also incorporated into RUES2 hESC.

Other embryonic cell lines having a wild-type HTT gene could have been used instead and genetically modified as described herein to create modified hESC cell lines and isogenic controls. In addition, three unmodified isogenic cell lines were generated with a normal allele 20 CAG codons) as a control.

The insert length (to create a 150Q HTT gene) was chosen to model the early-onset juvenile form of HD, which represents the worst case of the disease, in order to maximize the chances to discover possible differences. (As it turned out, this high number of polyQ was not necessary although it served the purpose.) For lineage tracing and selection purposes, a mCherry-blastidicine cassette flanked by self-cleaving peptide 2A sites upstream of the start codon was inserted (FIG. 1A). Successful modification of the locus was confirmed by PCR. The resulting RUES2-Q150 cells were karyotypically normal and expressed both HTT alleles, as evidenced by Western blotting of cell lysates for HTT. It is anticipated that expression of one HTT allele would have been sufficient to display the HD phenotype. Expression of mCherry was confirmed using fluorescent imaging.

To show that the genome editing strategy did not affect the basic properties of hESCs, it was confirmed that, when grown under pluripotency conditions (which can be checked by testing for expression of one or more pluripotency markers such as POU5F1 (a/k/a OCT4), SOX2, NANOG, LIN28A, LIN28B, and DNMT3, all of which were tested here). RUES2-Q150 cells maintained normal hESC morphology, and expressed pluripotency markers for example at levels similar to wild type RUES2 cells (FIG. 1B). In addition, the rate of cell proliferation by EdU incorporation was examined, as well as the rate of apoptosis by activated Caspase-3 immunostaining, and no differences were found between the two lines.

Finally, to determine the differentiation potential of these cells toward a lineage that is relevant to HD, dual-SMAD inhibition comprising SB431542 and LDN 193189 was used to induce neuronal fate by default. Alternatively, a combination of SB (SB431542) and Noggin could have been used instead to induce neuronal fate. RUES2-Q150 cells formed rosettes of typical morphology expressing the neuronal-specific markers PAX6 and N-Cadherin. Other differentiation markers were also expressed, such as SOX17, EOMES, T (BRA), CDX2, FOXA2 and FOXG1. Any one of these markers would have been enough to show differentiation. However, if all are revealed, the various germ layers can be visualized and differentiation in each layer can be assessed. Taken together, these results demonstrate that the genome editing did not change the basic properties of isogenic hESCs.

IB. Generation of ESCs Spanning a Various Range of polyCAG Lengths Found in HD Patients without Detectable and Selectable Markers In addition to HD ESC lines spanning various polyQ lengths of HTT gene and comprising detectable marker (expression marker) mCherry and blastidicine cassette, the Applicants also generated cells that comprise various polyQ lengths, but lack the detectable marker and selectable marker cassettes. The present inventors generated a set of >400 ESC lines spanning the typical range of polyCAG lengths found in HD patients 42, 48, 56, 67, and 150 CAGs (FIG. 13A). RUES2 hESC line was again used as the parental line. All of the codons were CAG except for the penultimate one which was CAA, as it occurs in nature. However, a mixture of CAG and CAA codons could have been used as was done for the 150Q modified cells. Briefly, cells were generated using CRISPR technology as described in Materials and Methods below. In order to generate cells in which polyQ tract is the same as the one found in HD patients (comprising essentially only CAG repeat), the inventors used a PCR to amplify a mutant Huntington's gene locus directly from patient samples using the following cells: ND38548 from the Coriell Insititute, GENEA020 from GENEA Biocells, and QS-001 and QS-004 fibroblasts from the Tabrizi laboratory (United Kingdom). These cells were used as starting material for PCR to make the donor plasmid. Fibroblasts are available from many public and commercial sources and these could have been used instead. The same is true for the remaining cells: they are available from alternative sources. The polyQ tract comprising only CAG trinucleotide can also be synthesized in the lab.

Additionally, the Applicants used a selectable marker that contained an ePiggybac transposable element, which allowed marker removal once the selected cells were identified. The excision-only trasnposase was purchased from Transposagen (Lexington, KY 40508). Thus, ultimately, these cells do not comprise a selectable marker, and differ from isogenic wildtype control cells only in the length of the polyQ tract. Importantly, all of these modified cell lines exhibited the disease phenotype.

Given that these cells have fewer differences when compared to isogenic normal control cells than the cells comprising expression marker and selectable marker cassette, they provide another set of embodiments for modeling Huntington Disease, which is essentially devoid of inserted sequences except for the introduced polyQ tract.

6.1.2. Discussion 6.1.2.1. Signature of HD in an HD Model Organoid

Figure 3A:
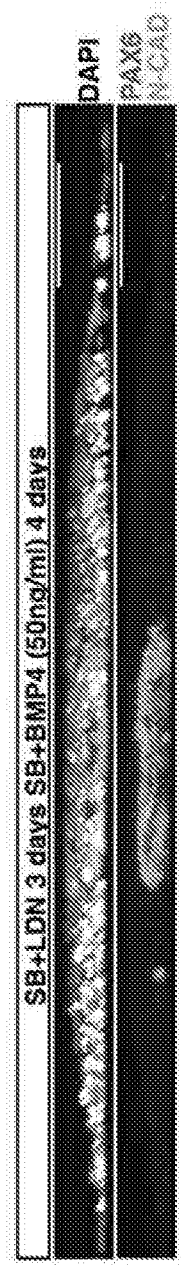
Figure 3B:
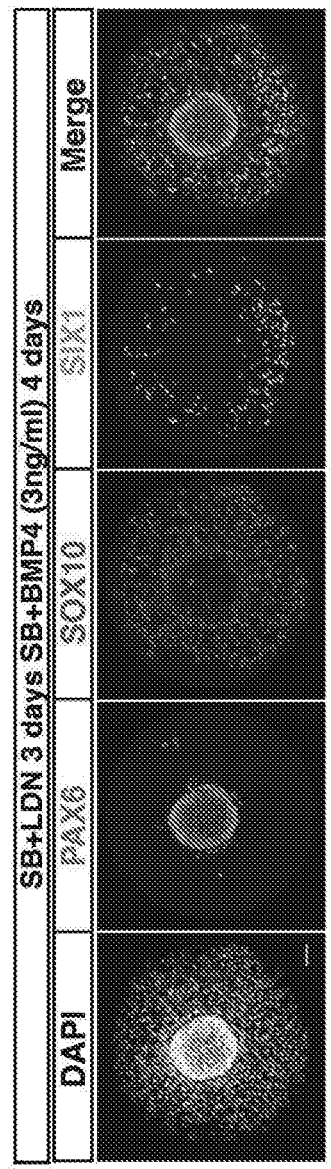
Figure 3C:
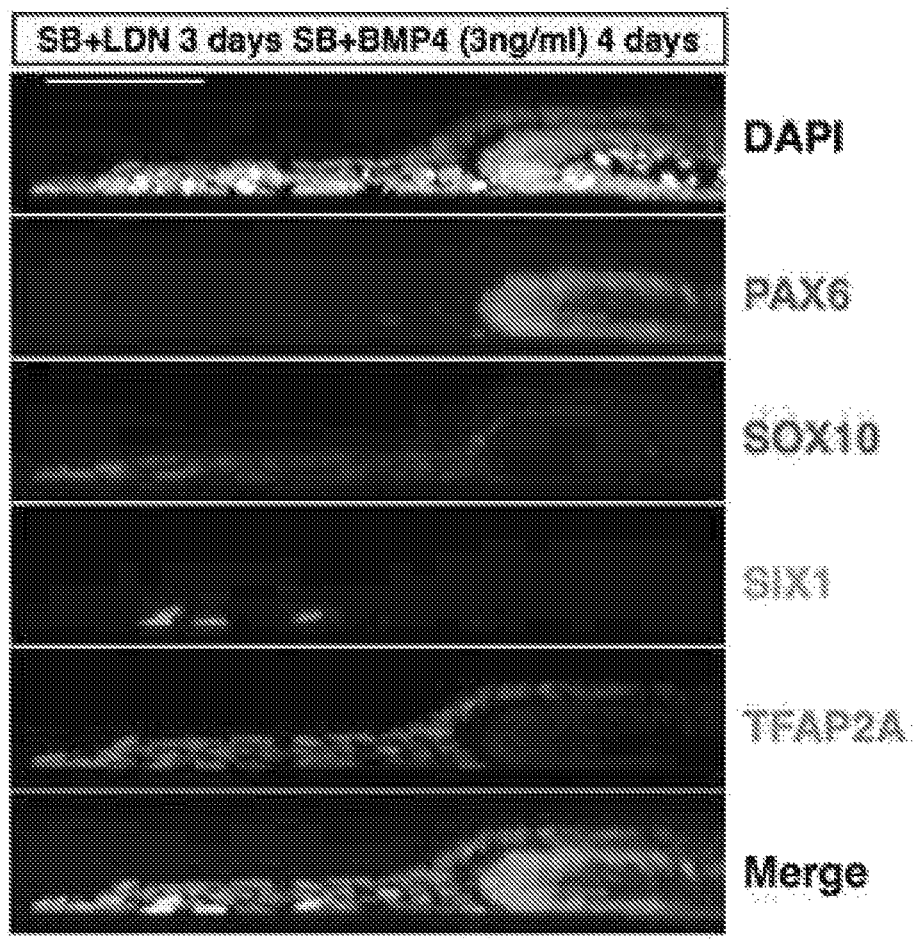
Figure 3D:
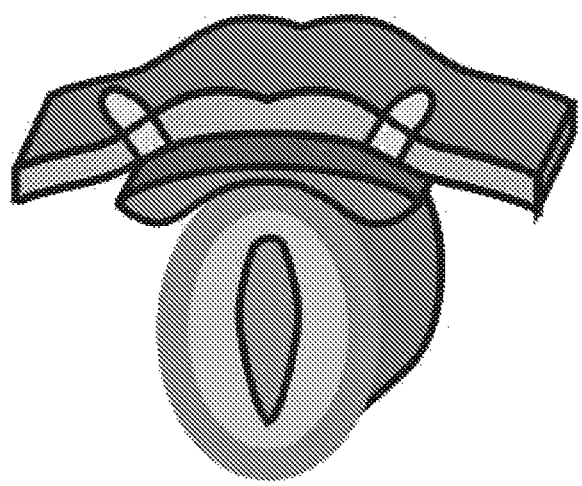
Figure 3E:
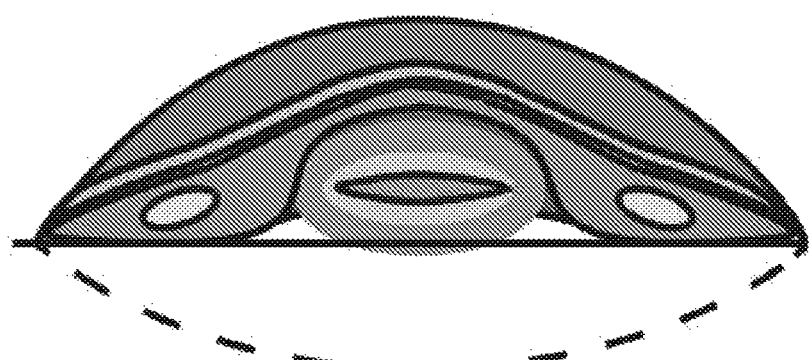

Neurulation is one key developmental transition during which the central nervous system is positioned. Micropattern cultures coupled to a specific induction protocol can lead to the formation of self-organized cellular assemblies that reconstitute the ectodermal compartment at neurulation stages. These reconstituted embryonic parts show a developing central nervous system organized into a neural rosette at the center (PAX6+ cells, in green, FIG. 3), together with neural crest (SOX10+, red population) and placode fates (SIX1+, yellow cells), covered by a layer of epidermis cells (TFAP2+ only, in blue). The comparison of the in vitro neurulation organoid model with the in vivo counterpart (FIGS. 3D-3E) shows a high level of similarities, thus making the HD organoid model assay an ideal endpoint for the study of human genetic disorders.

Figure 4A:
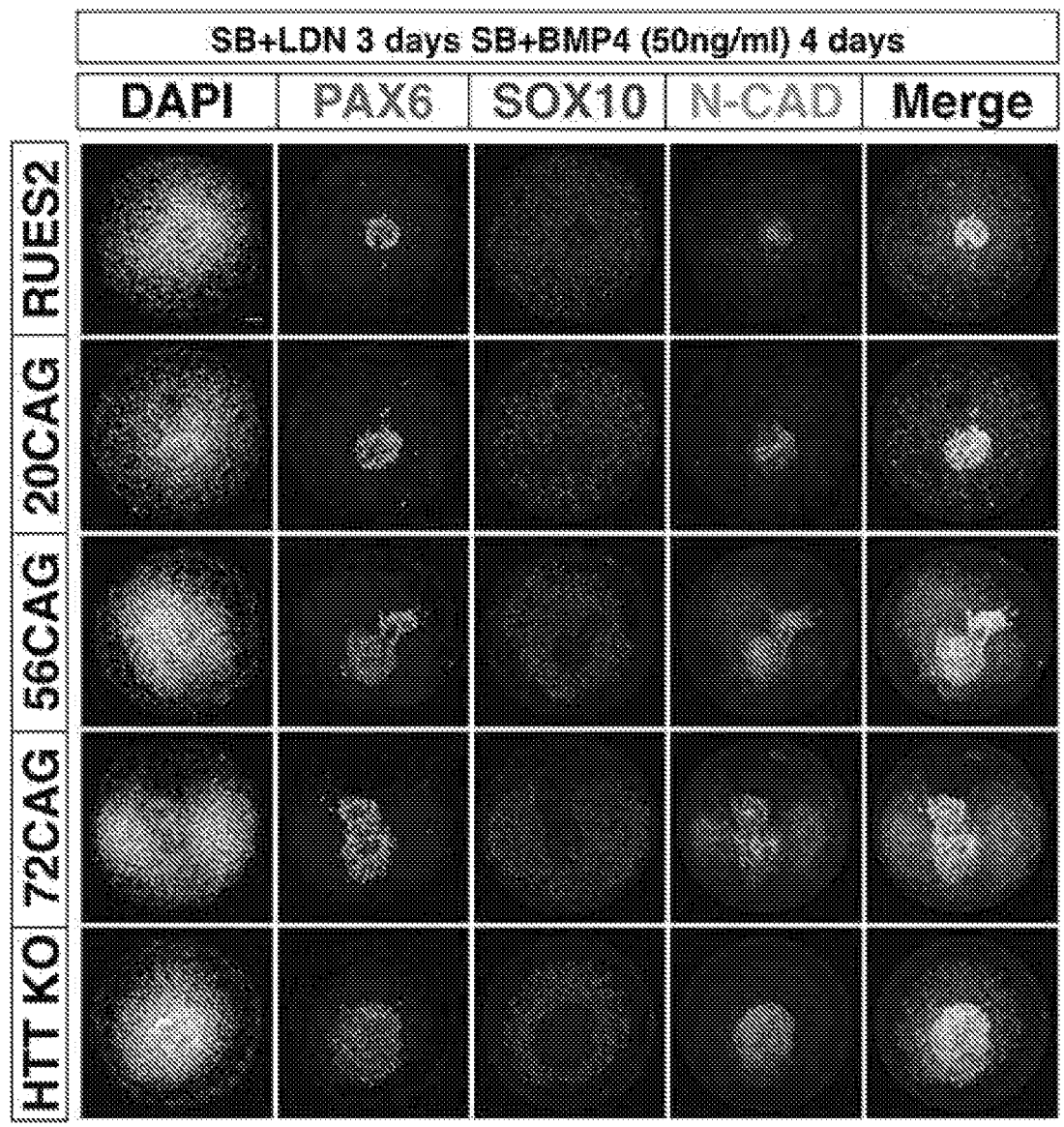
Figure 4B:
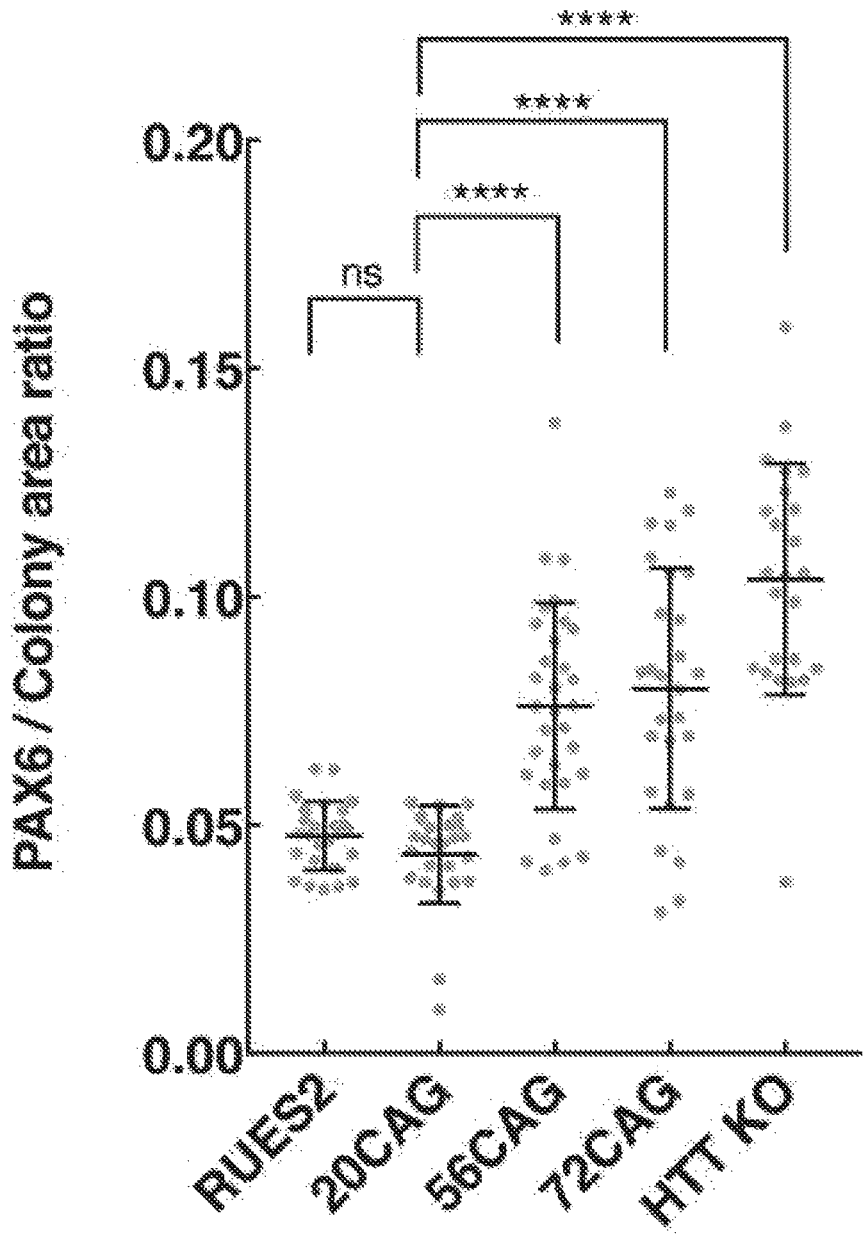

The emergence of large numbers of homogenous stereotypical self-organizing organoids prompted us to ask if they can be used to model Huntington's Disease (HD) because it has been linked to neuroepithelial morphogenesis. We thus used HD model organoids by using a series of HD isogenic hESCs lines and extracted one main feature: the PAX6 area. As shown in FIGS. 4A-4B, CAG extension was associated to increased PAX6+ area. Interestingly, the HTT−/− line showed the most dramatic phenotype.

6.1.2.2. Observing the HD Model Organoid Phenotype in 96 Well Plates

Figure 5B:
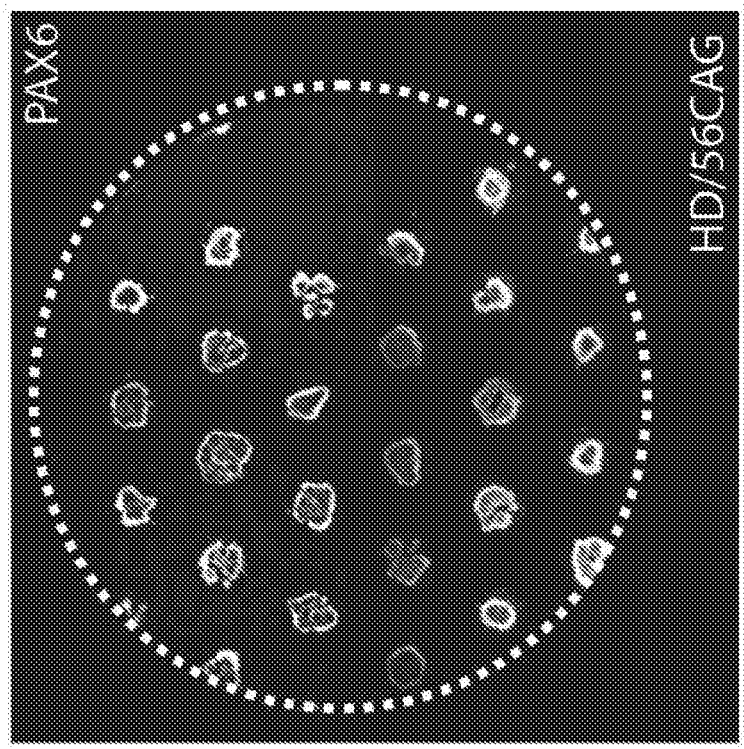
Figure 5A:
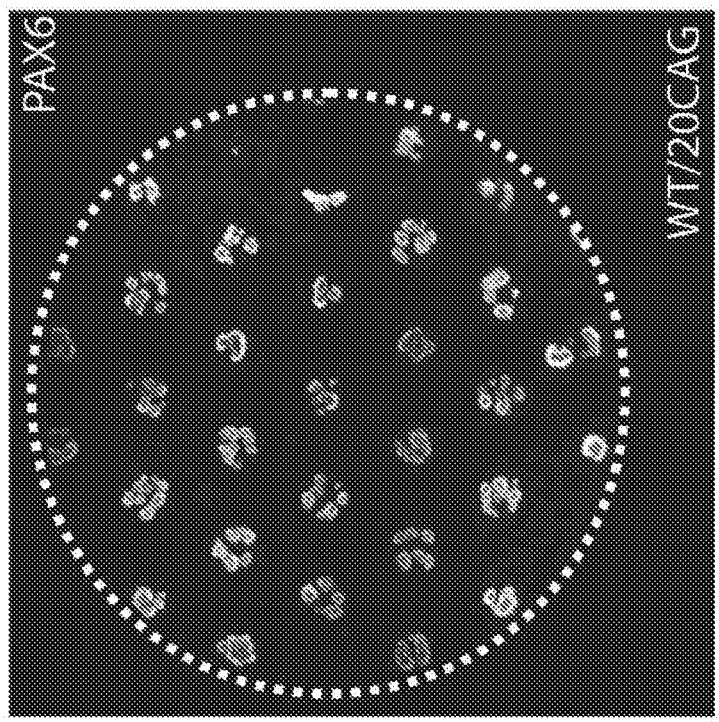
Figure 5C:
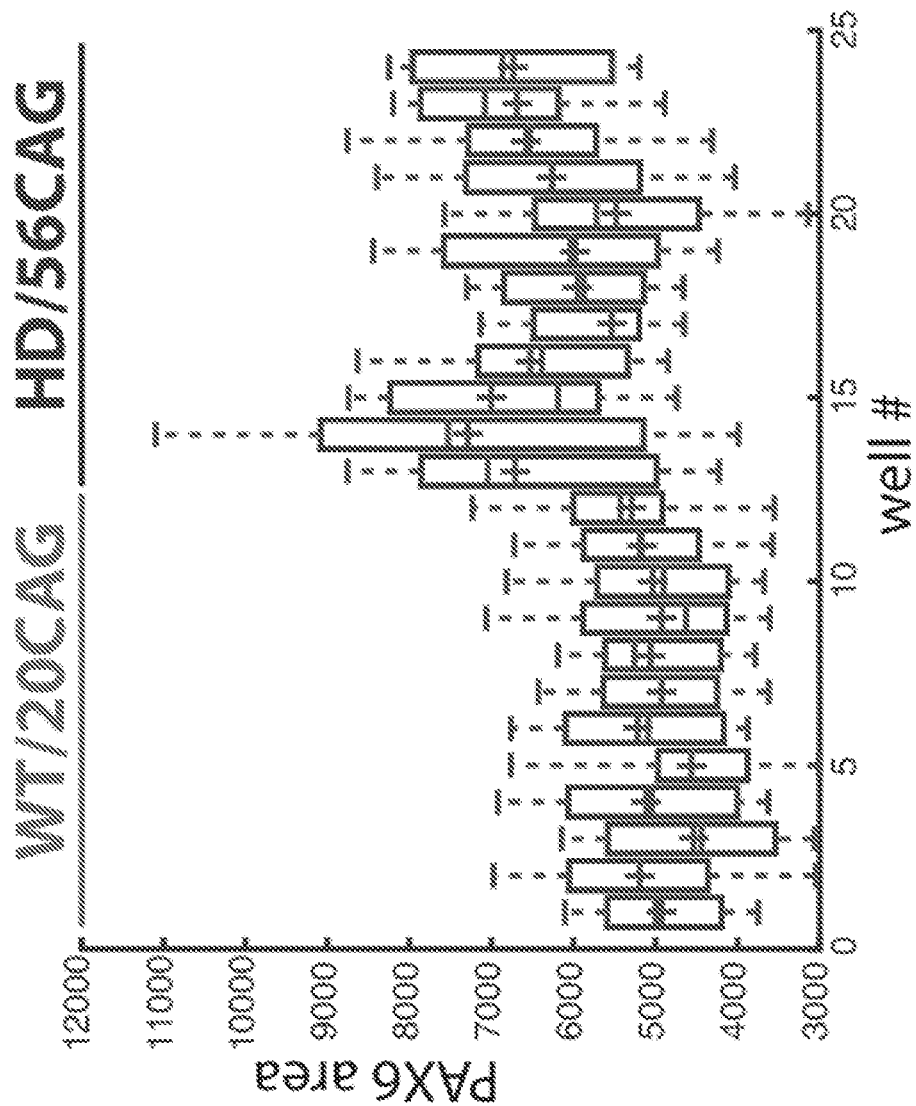

HD model organoid formation was adapted for micropatterned 96-well plates. HD-specific organoid phenotype was observed reproducibly in 96 well plates, with an average of 28 HD model organoids per well (FIG. 5). HD model organoids formed with the HD genetic background (FIG. 5B) had significantly larger PAX6+ domains than the WT hESC (FIG. 5A). A standard threshold-based analysis scheme was used to segment individual PAX6+ domain in each colony. FIG. 5C shows an example of quantification for multiple wells of the WT and HD background. Consistent with previous results, the HD-specific organoid phenotype was observed in 96 well plates: PAX6+ areas were significantly larger in the HD background than in the WT. Thus, the HD model organoid formation protocol was successfully adapted to 96-well plates, giving the ability to screen compounds for phenotypic reversal in a high-throughput screening campaign.

6.1.2.3. Screen Robustness: Z' Factor Calculation

When performing a High-throughput screen (HTS), a robust assay is needed in order to avoid high rates of false positive and false negatives. This implies a strong separation between positive and negative control. The tool widely used by the HTS community to measure assay robustness is the Z' factor. In the ideal case of an extremely large separation between positive and negative controls, Z' converges towards a value of 1. It is widely acknowledged that a good screen assay should have a Z'>0.5 to be robust enough for constituting a good screening platform, while Z'>0 is accepted in the case of a complex phenotypic screen. Negative values means that the assay cannot be the basis of a screening campaign.

Figure 6A:
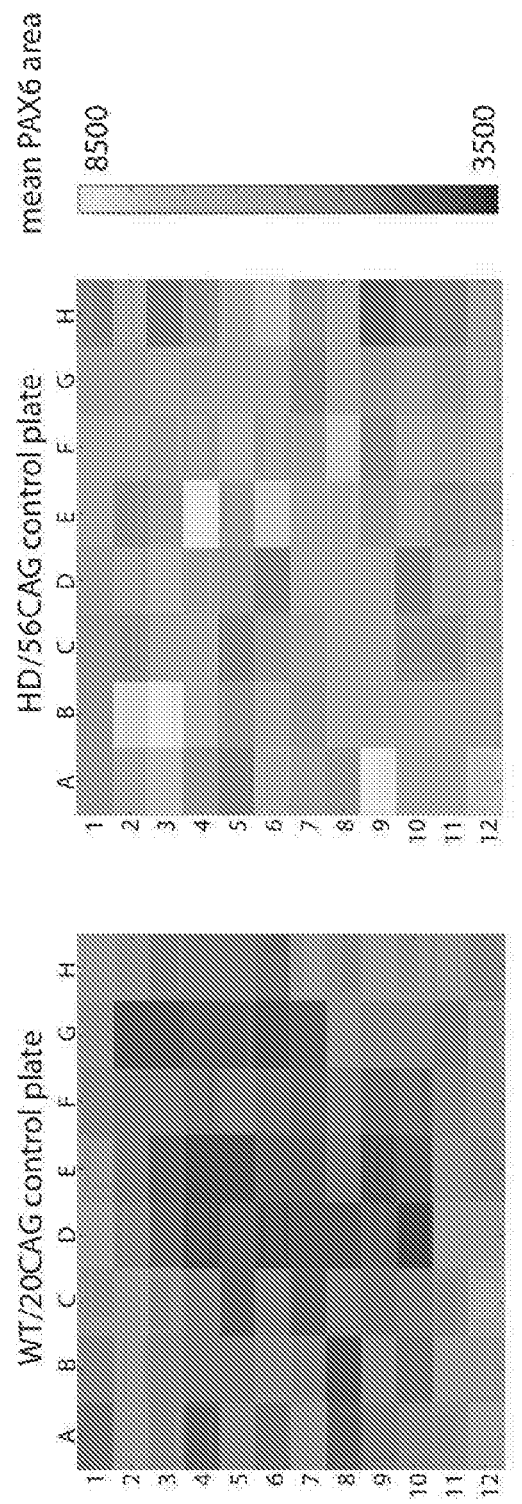

In order to measure the Z' factor, mean PAX6+ areas in control 96-well plates of the two different genetic backgrounds were quantified. Overall, it was observed that the WT/20CAG control plates had larger PAX6 positive areas than the HD/56CAG plates (FIG. 6A). The Z' factor associated with the assay in each well was then measured. For every well positioned at row r and column c, the following was measured:

$$Z'(r, c) = 1 - 3\frac{(std(PAX6\text{area}(r, c)_{HD-56CAG}) + std(PAX6\text{area}(r, c)_{WT-20CAG}))}{|mean(PAX6\text{area}(r, c)_{HD-56CAG}) - }$$

Figure 6B:
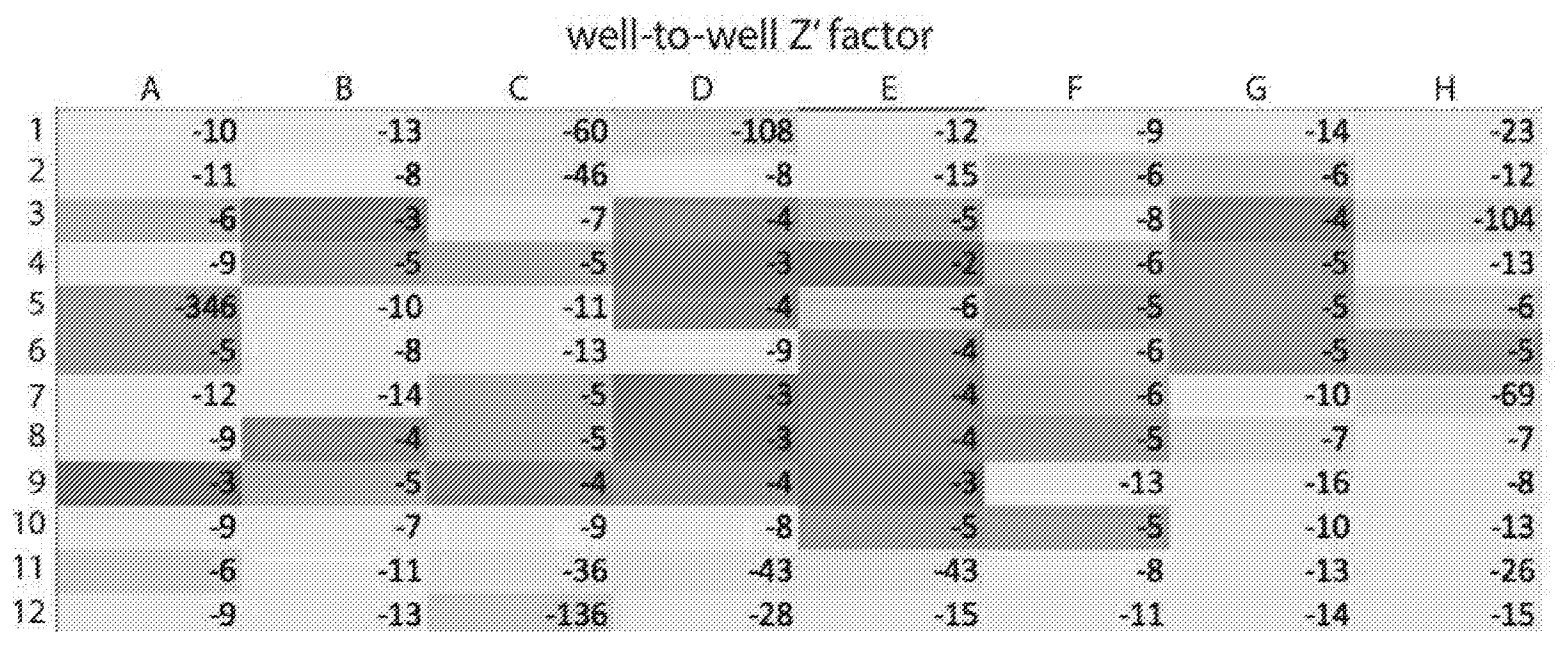

When this calculation was performed (FIG. 6B), it was realized that 1) the separation between positive and negative control is not good enough to obtain positive Z' scores and 2) there was a noticeable edge effect with the best Z' scores obtained at the center of the plate and the worst at the edges. However, a positive value was not achieved and the mean Z' for the full plate was −17. It was therefore decided to use a different analysis scheme to obtain positive Z' factors.

6.2. Example 2: Training a Neural Network to Recognize HD Organoids

It was noticed that while the quantification shown in FIG. 5C shows a large spread of the data and a small separation of the positive and negative controls, the differentiation between the WT and the HD phenotype seemed obvious to the human eye (FIGS. 5A-5B). This is because the human brain performs the complex task of image recognition not only by comparing a unique feature like the PAX6 area as quantified in FIG. 5C, but integrates many others: shape of the domain, relative intensities, and many other feature we are not even aware of. A machine learning approach was used to reconstitute this process computationally.

Deep neural networks have been heavily used for unbiased image classification over the past few years. For example, after building complex neural networks that were trained on annotated image databases, Google image is now able to classify as "cat" a picture of a cat it never saw before. It was hypothesized that a similar approach could be used for phenotypic analysis, and to improve the robustness of screening technology. A computer equipped for GPU computing and a publically-available deep neural-network architecture were used as a starting point.

Figures 7A, 7B:
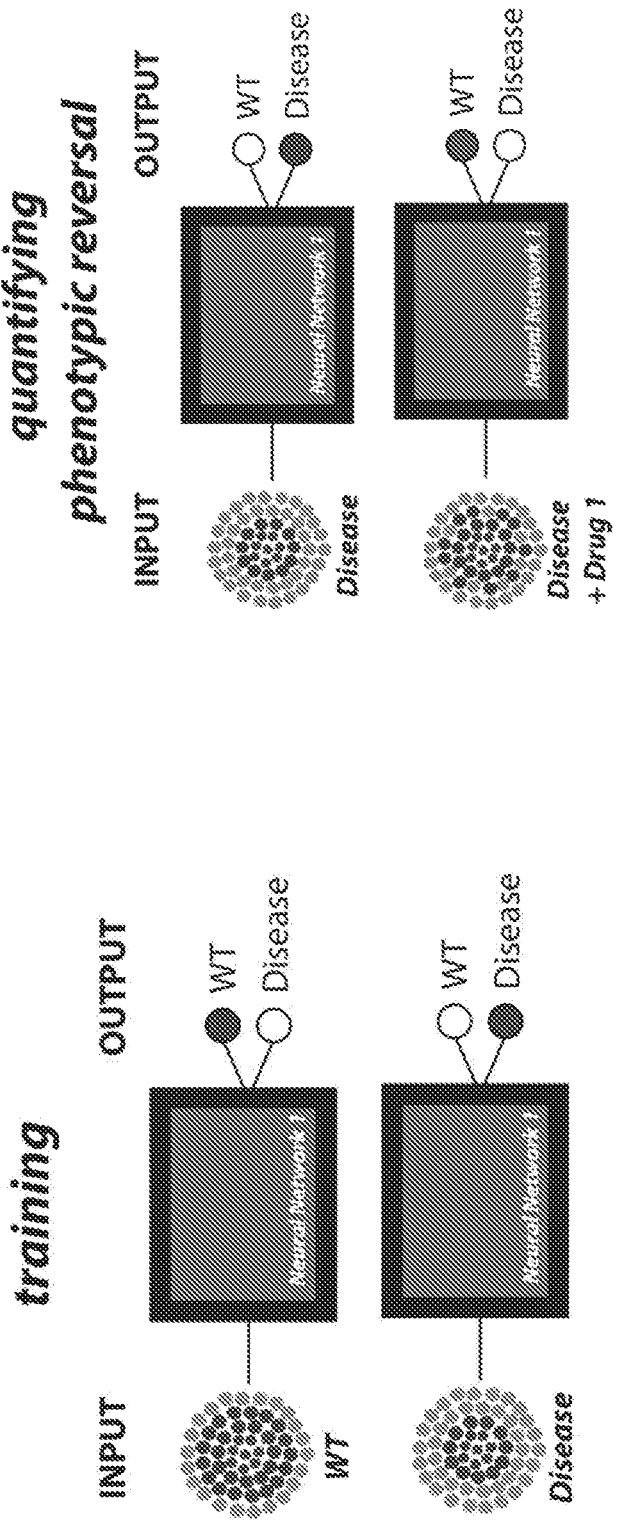

The strategy used can be described in two steps. In a first training phase (FIG. 7A) the network would be shown a set of images belonging to the WT and the HD background obtained in control conditions. At the end of the training, the network has learned to recognize both phenotypes and would be able to classify accurately previously unseen images as coming from the WT or the HD background. In a second phase, the trained network would be used to analyze the results of our screening campaign by querying the networks with images from the screen. While diseased HD organoids treated with DMSO would be classified as belonging to the HD class by the network, hit compounds reverse the phenotype back to WT and images would be now classified as WT (FIG. 7B).

Figure 8A:
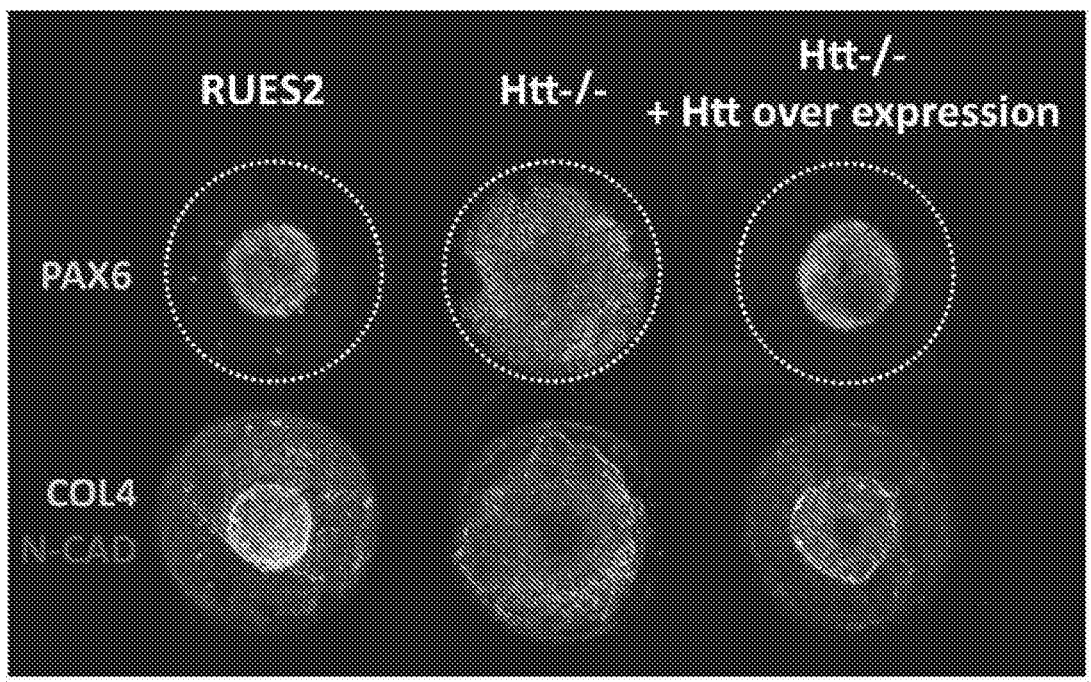
Figure 8B:
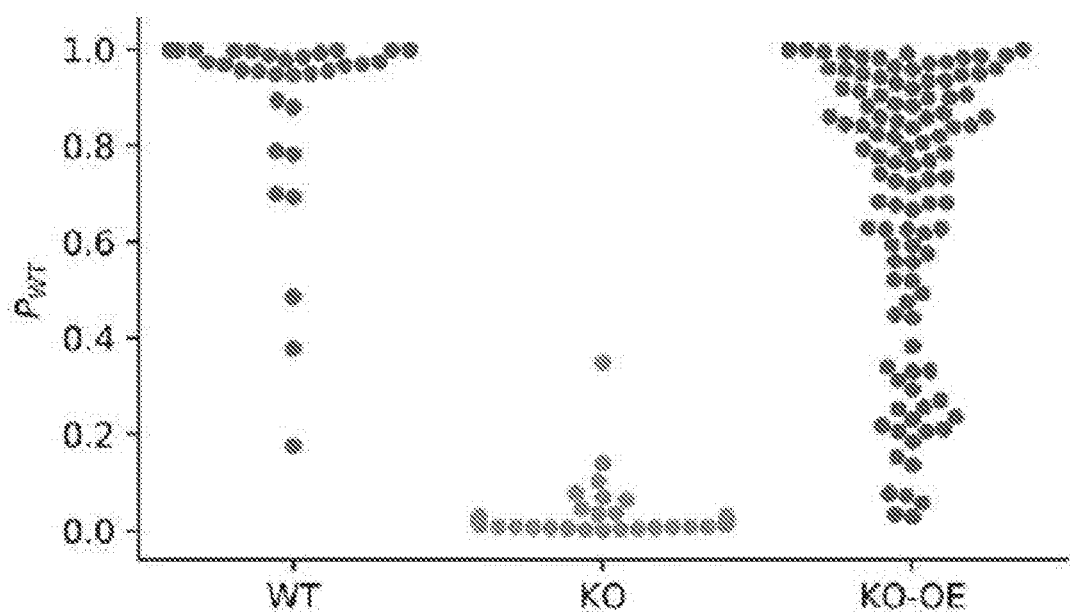

In a first proof of concept, we attempted to train the network to efficiently recognize WT and Htt−/− HD model organoids, (FIG. 8A), as our initial work had shown that the most dramatic HD phenotypes are obtained in the Htt−/− background (FIG. 4). The network was trained on 400 WT HD model organoid images and 400 HD HTt−/− HD model organoid images. When we showed the network previously unseen WT or Htt−/− HD model organoid, it was able to classify them accurately to the correct class with a precision of 97%. This result is shown in FIG. 8B. Importantly, the network is able to tell whether a new queried image belongs to the WT class or HD class of images. In a further step, in order to prove that the tool can be used for analyzing phenotypic reversal, the Htt gene was re-expressed by over-expression on top of the Htt−/− background in a separate cell line, with the rationale that a rescue of protein expression would rescue the HD model organoid phenotype. When images of HD model organoid of the Htt−/− background with Htt over-expression were queried to the network (FIG. 8B), they were classified with higher probability as belonging to the WT class, therefore quantitatively demonstrating phenotypic rescue.

6.3. Example 3: High Throughput Screening of a Compound Library for Reversion of the HD Phenotype The network was applied to a high-throughput screening campaign aimed at finding compounds that reverse the HD phenotype. HD model organoids were prepared from isogenic WT hESCs and HD hESCs as described above in micropatterned 96 well plates. Multiple positive control plates with WT cells, and multiple negative control plates with untreated 56CAG HD line were prepared. Compounds were then added to the wells of 96 well plates containing the 56CAG HD line.

Figure 9:
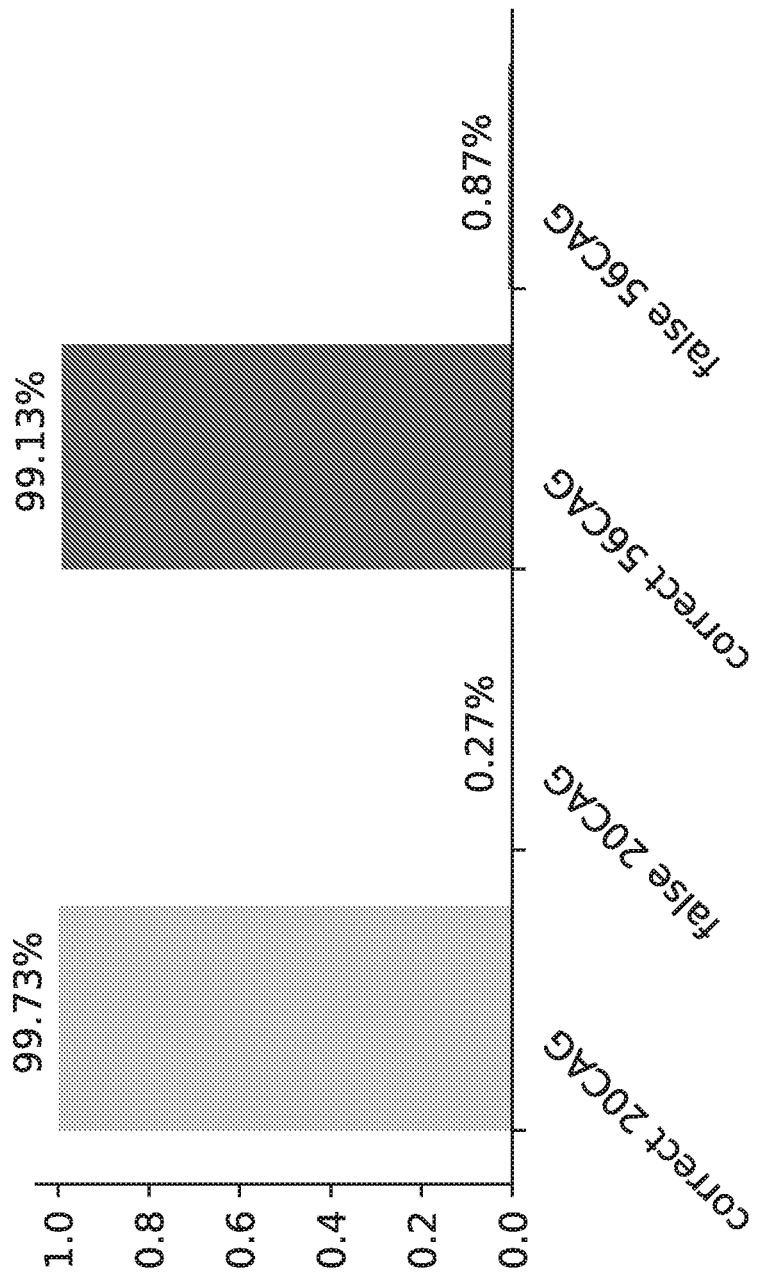

It was first tested whether the robustness of the assay as quantified by the Z' factor could be enhanced. HD model organoid from the control wells (WT and HD) were each randomly split into training and validation sets with proportion 70% and 30%, respectively, so that there were 67 training wells each and 29 validation wells each, with each well consisting of approximately 25 organoids. A neural network was then trained on the training set as described in the methods section, with 1750 WT and 1691 HD images. The trained network was evaluated on the validation set. The accuracy in classifying individual images is shown in FIG. 9.

Figure 10B:
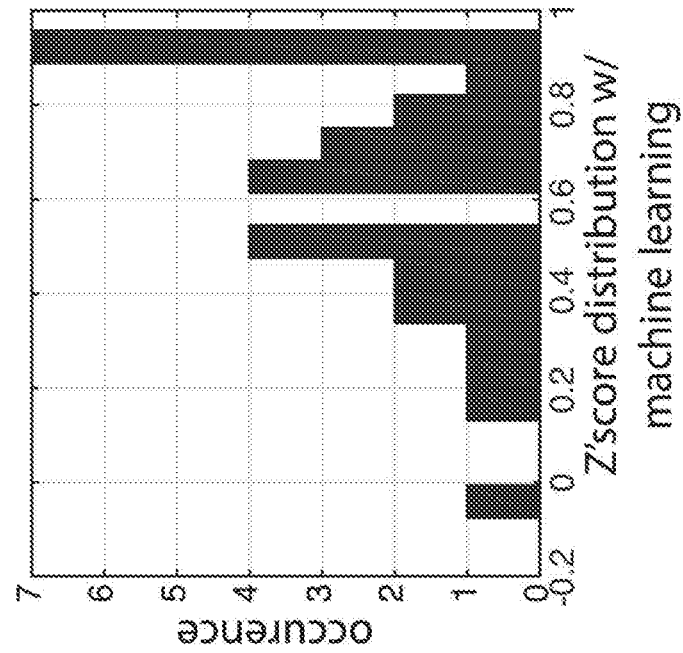
Figure 10A:
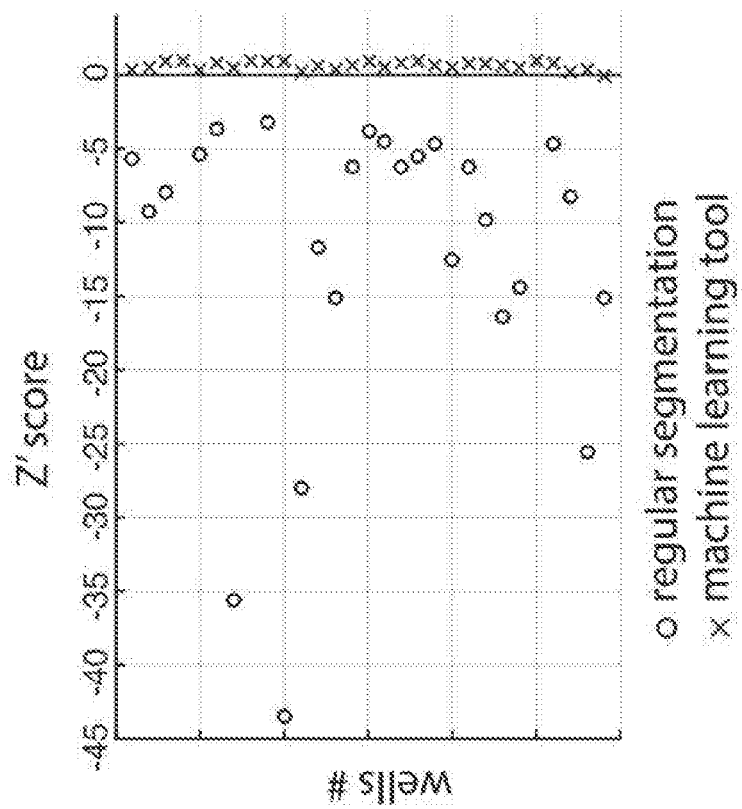

We then used our machine learning approach to test whether it could enhance the robustness of our assay as quantified by the Z' factor. The pilot experiment in multi-well plates was revisited with the neural network approach, and the Z' factor for different wells of the 96-well plate was calculated. A spectacular improvement of the screen quality was observed (FIG. 10A), with the Z' factor that was highly negative using the former segmentation-base method now becoming positive. A closer inspection of the Z' factor per well (FIG. 10B), demonstrated that most Z' factor were above 0.5 and all of them were positive. Only one well showed a slightly negative Z', but this is not highly important as this well corresponded to a plate corner well that served as a control well during the actual screen, as well as the first and last rows of the plates. Besides this particular well, all Z' values were positive, independent of whether the well was at the edge or at the center of the plate. Therefore, the innovative machine learning toolbox described herein allows the analysis of the HD specific phenotypic screen, with ideal conditions for finding hit molecules.

Figure 11:
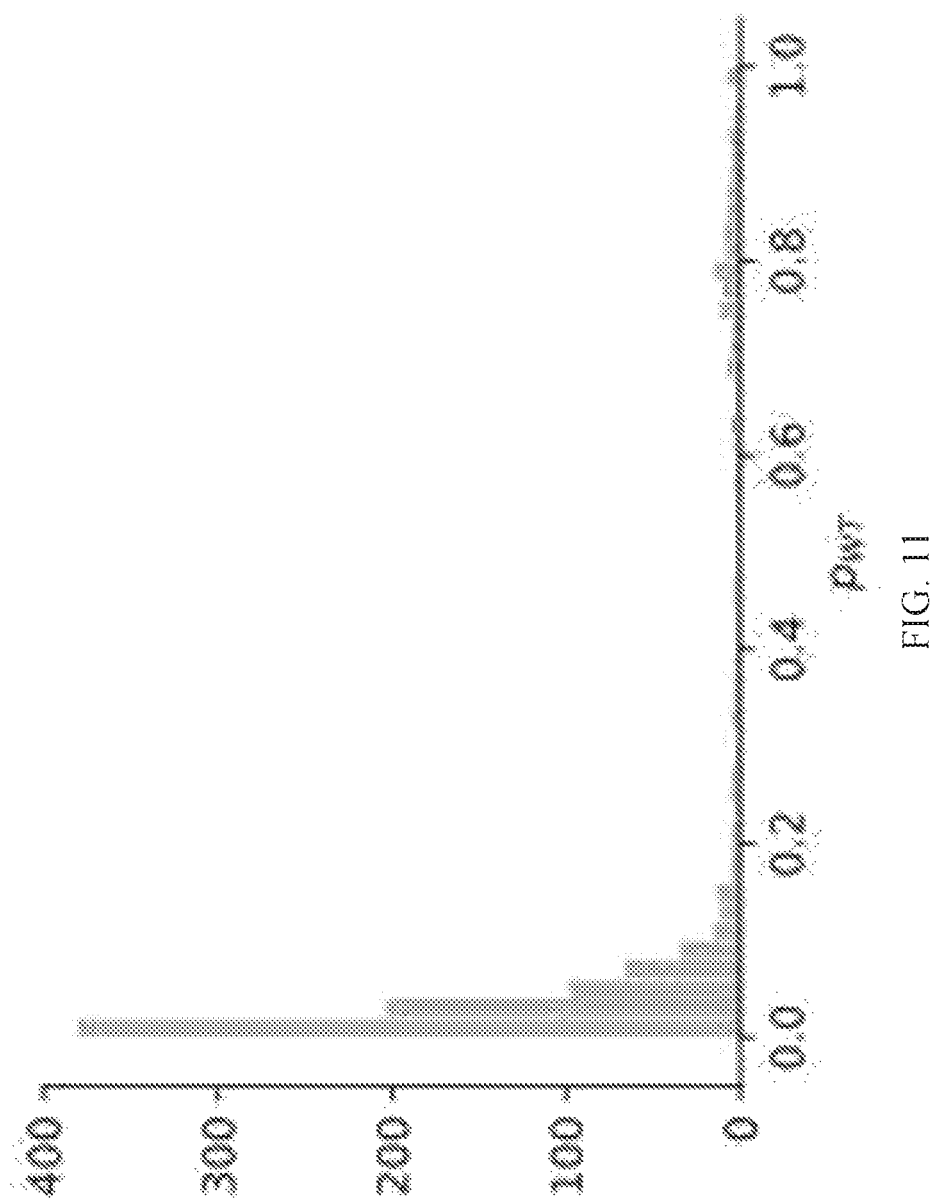
FIG. 11 shows distribution of the probability of each compound to revert the HD disease phenotype to WT, indicated as $p_{wt}$. Most compounds did not change the disease phenotype, but a low broad peak close to 1 indicated some compounds successfully revert the disease phenotype.

A screening campaign of 800 molecules was then performed. One control plate of WT (RUES2) control and one HD/56CAG control plate were included in order to train the neural network on this specific data set. In all other plates, HD/56CAG organoids (HD model organoid) were formed and compounds were applied. Wells with less than 10 intact organoids were excluded from the analysis, assuming that in those cases the compound had a toxic effect. For the others, the network measured, for each well, the capacity of compounds to reverse phenotypes based on the tools described in the previous section. For each HD model organoid, the network assigned a score, $p_{WT}$, between 0 (disease) and 1 (WT), which is the probability of a compound to reverse the disease HD phenotype back to the WT state. This score was then averaged across each well. A histogram of the resulting score per well is shown in FIG. 11.

As expected, most compounds did not change the HD/56CAG phenotype, and their associated probability to belong to the wild type class, $p_{wt}$, was close to the zero, which means that they were unaffected and still recognized by the network as belonging to the HD class. However, a few compounds were able to show phenotypic reversal and bring the probability to belong to the wild type class, $p_{wt}$, closer to one. Even more interestingly, 13 compounds had $p_{wt} > 0.95$.

6.4. Example 4: Analysis of Toxicity

Figure 12A:
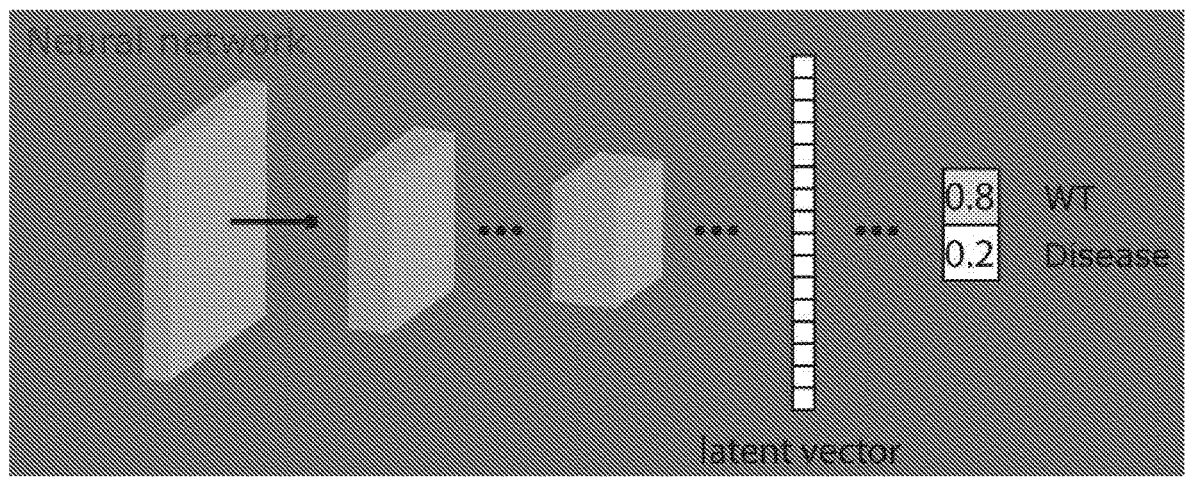
FIGS. 12A-12B show illustrations of an exemplary network architecture, with a fully connected latent vector upstream of the final classification layer (FIG. 12A) and t-SNE clustering of latent vectors corresponding to control wells and wells treated with compounds (FIG. 12B).

The relatively high number of hits in the screen of Example 3 prompted us to ask whether some false positive compounds could appear in the hit list due to the fact that the network is tied to two classes only, WT and HD. We therefore decided to extract from the network a third class of toxic compounds, which create an adverse effect on the HD model organoids and make them look like neither like the WT or HD phenotype. Those compounds rather make the HD model organoids completely different, which is a sign of toxicity. We therefore used our previous network, which has as output a binary choice between WT and HD, but where we extracted the fully connected layer upstream of the two last neurons. This layer has 512 neurons whose activity can be interpreted as a 512-dimensional latent vector, which allows a representation of each phenotype in the same latent space, and quantify how two phenotypes are different from each other. The network with the latent vector is illustrated in FIG. 12A.

Figure 12B:
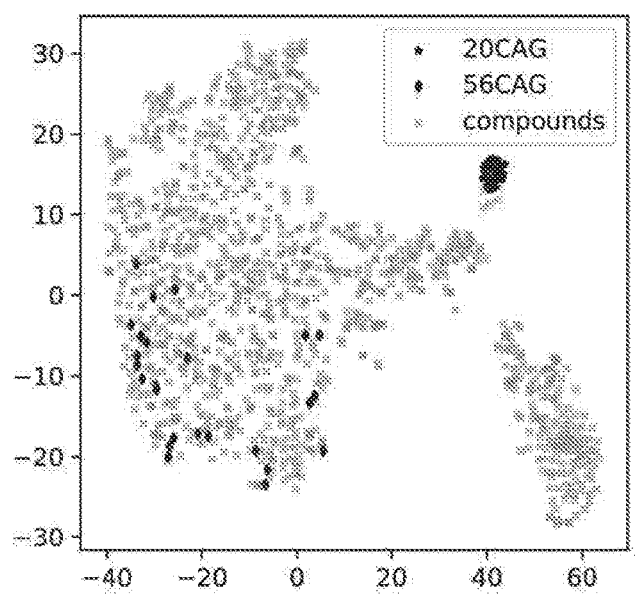

Using this network architecture, the effect of each compound was decomposed into two relevant components: its toxicity levels and its therapeutic potential. Therapeutic potential was measured by the output of the two WT and disease neurons as exemplified in FIG. 11. Toxicity was measured by assessing the difference between the compound treated colony and the two control phenotypes WT and disease. This degree of difference was calculated by taking the minimum of the difference between the latent vector associated with the compound treated colony and the latent vectors associated with the two controls. This could have been done on the full 512-dimensional latent space. However, it was advantageous to first reduce the dimensionality of the vectors so as to extract only the most relevant information encoded in the vectors, using e.g. t-distributed stochastic neighbor embedding (t-SNE) or principal component analysis (PCA). The difference of the vectors was then calculated on the reduced space. The t-SNE clustering of the vectors corresponding to control and treated wells is shown in FIG. 12B.

For optimal display of the results, the effect of each compound was plotted on a triangle shaped phenotypic map as illustrated in FIG. 13.

When this methodology was used to plot the results of the screen (FIG. 14), five compounds that have high therapeutic potential (they clustered in the WT corner of the plot, showing high phenotypic reversal) as well as low toxicity (they remained at a distance from the toxic corner of the triangle) were found.

6.5 Example 5: Analysis of Toxicity by Way of Autoencoders

A convolutional autoencoder based method was used to assess toxicity. These unsupervised neural networks encode data and compress it in a low dimensional latent representation (FIG. 15).

The unsupervised nature of this machine learning method has the advantage that the autoencoder learns a representation of the data without any additional information about the data (such as that it is derived from wild type or disease cell lines), and is thus unbiased in estimating the toxicity of compounds. The representation of the data in terms of vectors also has the advantage that differences in the wild type and disease phenotype can be removed from the vector space, since this difference is not relevant in determining toxicity. Toxicity was determined in the following way: First, the difference between wild type and disease is removed from the latent space. Then, the distance from the mean vector of the wild type and disease phenotypes is calculated, and compared to the standard deviation of the wild type and disease phenotypes. This distance is defined as the toxicity (FIG. 16).

The accuracy of this method was tested by applying drugs with known toxic effects at different concentrations, and comparing the results to a conventional colorimetric "MTT" assay of cell viability performed using 56CAG RUES2 cells (here, viability is defined as the inverse of toxicity). The comparison shows consistent results and validates the autoencoder method for determining toxicity (FIG. 17).

7. SPECIFIC EMBODIMENTS

The present disclosure is exemplified by the specific embodiments below.

1. A method for classifying a test organoid, said method comprising the steps of: imaging a test organoid to provide an organoid image;
analyzing the organoid image with a trained neural network that has been trained to assign a classification to the test organoid, wherein the classification comprises disease phenotype or non-disease phenotype.
2. The method of embodiment 1, wherein the cells of the organoid having a disease phenotype comprise one or more mutations that confer the disease phenotype.
3. The method according to any one of the previous embodiments, wherein the cells of the organoid having a non-disease classification and disease classification are isogenic.
4. The method according to any one of the previous embodiments, wherein the organoid comprises multicellular aggregate, stem cell, pluripotent cell, induced pluripotent cell, human embryonic stem cell, adult stem cell, totipotent stem cells, or non-embryonic cell.
5. The method according to any one of the previous embodiments, wherein disease comprises Huntington's disease.
6. The method according to any one of the previous embodiments, wherein imaging comprises staining the organoids for one or more markers.
7. The method according to embodiment 6, wherein the one or more markers comprise organelle markers, cell differentiation markers, cell compartment markers, or combinations thereof.
8. The method according to any one of embodiments 6-7, wherein the one or more markers comprises a nuclear marker.
9. The method according to any one of embodiments 6-8, wherein the one or more markers comprise a membrane marker.
10. The method according to any one of embodiments 6-9, wherein the one or more markers comprise a cell differentiation marker.
11. The method according to any one of embodiments 6-10, wherein at least two images of each organoid are analyzed, each corresponding to a different marker and a different color channel.
12. The method of any one of embodiments 6-11, wherein at least three images of each organoid are analyzed, each image corresponding to a different marker and a different color channel.
13. The method of any one of the preceding embodiments, wherein the organoid image comprises a two-dimensional image.
14. The method of any one of the preceding embodiments, wherein the organoid image comprises a three-dimensional image.
15. The method according to any one of the preceding embodiments, wherein the trained neural network is a neural network trained with a plurality of images of organoids belonging a non-disease classification and images of organoids belonging to a disease classification, wherein said neural network comprises a plurality of layers and a last layer comprising two nodes.
16. The method according to embodiment 15, wherein the neural network comprises a fully connected layer upstream of the last two nodes, said fully connected layer comprises at least 10 nodes.
17. The method according to embodiment 15, wherein the neural network comprises a fully connected layer upstream of the last two nodes, said fully connected layer comprises at least 100 nodes.
18. The method according to embodiment 15, wherein the neural network comprises a fully connected layer upstream of the last two nodes, said fully connected layer comprises at least 250 nodes.
19. The method according to embodiment 15, wherein the neural network comprises a fully connected layer upstream of the last two nodes, said fully connected layer comprises at least 400 nodes.
20. The method according to embodiment 15, wherein the neural network comprises a fully connected layer upstream of the last two nodes, said fully connected layer comprises at least 500 nodes.
21. The method according to embodiment 15, wherein the neural network comprises a fully connected layer upstream of the last two nodes, said fully connected layer comprises at least 600 nodes.
22. The method according to embodiment 15, wherein the neural network comprises a fully connected layer upstream of the last two nodes, said fully connected layer comprises at least 800 nodes.

23. The method according to embodiment 15, wherein the neural network comprises a fully connected layer upstream of the last two nodes, said fully connected layer comprises at least 1000 nodes.

24. The method according to any one of embodiments 15-23, wherein the neural network comprises a fully connected layer upstream of the last two nodes, said fully connected layer comprises 512 nodes.

25. The method according to any one of embodiments 1-24, wherein the fully connected layer upstream of the last two nodes is the penultimate layer.

26. The method according to any one embodiments 15-25, wherein analyzing further comprises:
extracting a fully connected layer upstream of the two last nodes; and
calculating a degree of difference.

27. A method for identifying a test molecule that is biologically active against a disease, comprising:
    (a) culturing a first mammalian cell population under organoid formation conditions to obtain a first organoid, wherein the organoid formation conditions include exposure to a test molecule, and wherein the first mammalian cell population, when cultured under the organoid formation conditions in the absence of a biologically active molecule, results in an organoid with a disease phenotype;
    (b) imaging the first organoid following exposure to the test molecule;
    (c) analyzing one or more images of the first organoid using a neural network that has been trained to assign a probability score of disease or non-disease ranging between 0% and 100%;
    (d) assigning the first organoid a probability score ranging between 0% and 100%;
wherein the test molecule is biologically active against the disease if the probability score of the first organoid is greater than a cutoff probability score of non-disease or lower than a cutoff probability score of disease.

28. The method of embodiment 27, wherein the first mammalian cell population contains one or more mutations that confer the disease phenotype.

29. The method of embodiment 27 or embodiment 28, which further comprises validating the activity of the test molecule against the disease.

30. The method of embodiment 29, wherein validating comprises determining the IC50 of the test molecule.

31. The method of embodiment 30, wherein measuring the IC50 of the test molecule comprises repeating the method of embodiment 27 using at least 3 different concentrations of the test molecule and analyzing the probability scores of disease or non-disease for different concentrations using a nonlinear least-square fit algorithm.

32. The method of embodiment 31, which further comprises selecting the test molecule for further analysis or development if it has an IC50 of less than 5 µM.

33. The method of embodiment 32, which comprises preparing derivatives of the test molecule in order to find a derivative with a lower IC50.

34. The method of embodiment 33, wherein the lower IC50 is lower than 100 nM.

35. The method of any one of embodiments 27-34, wherein the neural network has further been trained to assign a probability score of toxicity or non-toxicity ranging between 0% and 100%.

36. The method of embodiment 35, which further comprises assigning the first organoid a probability score of toxicity or non-toxicity ranging between 0% and 100%.

37. The method of embodiment 35 or embodiment 36, which further comprises determining the LC50 of the test molecule.

38. The method of embodiment 37, wherein determining the LC50 of the test molecule comprises repeating the method of embodiment 36 using at least 3 different concentrations of the test molecule and analyzing the probability scores of toxicity or non-toxicity for different concentrations using a nonlinear least-square fit algorithm.

39. The method of any one of embodiments 27 to 38, which further comprises determining the IC50 and LC50 of the test molecule and selecting for further analysis a test molecule that has a greater LC50 than IC50.

40. The method of embodiment 39, wherein the LC50 is at least 10 times greater than the IC50.

41. The method of embodiment 39, wherein the LC50 is at least 100 times greater than the IC50.

42. The method of any one of embodiments 27 to 41, which further comprises assaying the activity of the test molecule in an animal model of the disease.

43. The method of any one of embodiments 27 to 42, which further comprises verifying the accuracy of the neural network.

44. The method of embodiment 43, wherein verifying accuracy of the neural network comprises:
    (e) culturing a second mammalian cell population of the same cell type(s) as the first cell population under organoid formation conditions to obtain a second organoid that results in an organoid without the disease phenotype;
    (f) imaging the second organoid; and
    (g) assigning the second organoid a probability score ranging between 0% and 100%,
wherein the neural network is deemed to be accurate if the probability score of the second organoid is greater than a cutoff probability score of non-disease or lower than a cutoff probability score of disease;
or
    (h) culturing a second mammalian cell population of the same cell type(s) as the first cell population under organoid formation conditions to obtain a third organoid that results in an organoid with the disease phenotype;
    (i) imaging the third organoid; and
    (j) assigning the third organoid a probability score ranging between 0% and 100%,
wherein the neural network is deemed to be accurate if the probability score of the third organoid is lower than a cutoff probability score of non-disease or greater than a cutoff probability score of disease.

45. The method of embodiment 44, wherein the first mammalian cell population contains one or more mutations that confer the disease phenotype and wherein, other than said one or more mutations, the second mammalian cell population is isogenic to the first mammalian cell population.

46. The method of embodiment 44 or embodiment 45, wherein step (e) is performed concurrently with step (a).

47. The method of any of embodiments 27 to 46, wherein the first mammalian cell population is cultured in the presence of the test molecule for at least 3 days.

48. The method of any one of embodiments 27 to 47, wherein the concentration of the test molecule in the culture ranges between 10 nM to 100 μM.
49. The method of embodiment 48, wherein the concentration of the test molecule ranges between 1 μM and 20 μM.
50. The method of any one of embodiment 27 to 49, wherein the organoid formation conditions comprise culturing a mammalian cell population on micropatterns.
51. The method of any one of embodiments 27 to 50, wherein the first mammalian cell population is a population of stem cells.
52. The method of embodiment 51, wherein the stem cells are totipotent stem cells.
53. The method of embodiment 51, wherein the stem cells are human embryonic stem cells.
54. The method of embodiment 51, wherein the stem cells are pluripotent stem cells.
55. The method of any one of embodiments 51 to 54, wherein the organoid formation conditions comprise one or more differentiation factors in the culture medium.
56. The method of embodiment 55, wherein the differentiation factor is a neural differentiation factor.
57. The method of embodiment 56, wherein the neural differentiation factor is BMP4.
58. The method of any one of embodiments 27 to 57, wherein the first mammalian cell population encodes a Huntingtin protein with an expanded polyglutamine repeat.
59. The method of embodiment 58, wherein the expanded polyglutamine repeat contains 42-150 glutamine residues.
60. The method of embodiment 59, wherein the expanded polyglutamine repeat contains 42 glutamine residues.
61. The method of embodiment 59, wherein the expanded polyglutamine repeat contains 45 glutamine residues.
62. The method of embodiment 59, wherein the expanded polyglutamine repeat contains 48 glutamine residues.
63. The method of embodiment 59, wherein the expanded polyglutamine repeat contains 50 glutamine residues.
64. The method of embodiment 59, wherein the expanded polyglutamine repeat contains 56 glutamine residues.
65. The method of embodiment 59, wherein the expanded polyglutamine repeat contains 58 glutamine residues.
66. The method of embodiment 59, wherein the expanded polyglutamine repeat contains 67 glutamine residues.
67. The method of embodiment 59, wherein the expanded polyglutamine repeat contains 72 glutamine residues.
68. The method of embodiment 59, wherein the expanded polyglutamine repeat contains 74 glutamine residues.
69. The method of embodiment 59, wherein the expanded polyglutamine repeat contains 150 glutamine residues.
70. The method of any one of embodiments 27 to 69, wherein the first mammalian cell population is cultured in a microwell plate.
71. The method of embodiment 70, wherein the microwell plate is a 24-well microwell plate.
72. The method of embodiment 70 or embodiment 71, wherein the first mammalian cell population is cultured under conditions that produce 20-30 organoids per well.
73. The method of any one of embodiments 27 to 72, which further comprises staining the organoids for one or more markers.
74. The method of embodiment 73, wherein the one or more markers comprise organelle markers, cell differentiation markers, cell compartment markers, or combinations thereof.
75. The method of embodiment 74, wherein the one or more markers comprises a nuclear marker.
76. The method of embodiment 74 or embodiment 75, wherein the one or more markers comprise a membrane marker.
77. The method of any one of embodiments 74 to 76, wherein the one or more markers comprise a cell differentiation marker.
78. The method of any one of embodiments 27 to 77, wherein at least two images of each organoid are analyzed, each corresponding to a different marker and a different color channel.
79. The method of any one of embodiments 27 to 77, wherein at least three images of each organoid are analyzed, each corresponding to a different marker and a different color channel.
80. The method of any one of embodiments 27 to 79, wherein the images comprise two-dimensional images.
81. The method of any one of embodiments 27 to 79, wherein the images comprise three-dimensional images.
82. The method of any one of embodiments 27 to 79, wherein the probability score is given on a scale of 0 to 1.
83. The method of any one of embodiments 27 to 81, wherein the cutoff probability score is 95%.
84. The method of any one of embodiments 27 to 81, wherein the cutoff probability score of at least 85% is indicative of non-disease.
85. The method of any one of embodiments 27 to 81, wherein the cutoff probability score of at least 90% is indicative of non-disease.
86. The method of any one of embodiments 27 to 81, wherein the cutoff probability score of at least 95% is indicative of non-disease.
87. The method of any one of embodiments 27 to 81, wherein the cutoff probability score of at least 99% is indicative of non-disease.
88. A method of screening a collection of test molecules to identify a molecule that is biologically active against a disease, comprising performing the method of any one of embodiments 27 to 87 for each test molecule in the collection.
89. The method of embodiment 88, wherein the collection represents all or a portion of a small molecule compound library.
90. The method of embodiment 88 or embodiment 89, wherein the collection comprises 100 to 100,000 test molecules.
91. The method of any one of embodiments 88 to 90, wherein the test molecules are screened individually.
92. The method of any one of embodiments 88 to 90, wherein the test molecules are screened in pools.
93. The method of embodiment 92, which further comprises performing the method of any one of embodiments 27 to 87 on individual members of a pool that results in a probability score greater than a cutoff probability score of non-disease or lower than a cutoff probability score of disease.
94. The method of any one of embodiments 27 to 93, wherein the neural network is a convolutional neural network.

95. The method of embodiment 94, wherein the neural network is a residual network.
96. The method of embodiment 94 or embodiment 95, wherein the neutral network comprises 18 to 152 layers.
97. The method of embodiment 96, wherein the layers comprise convolutional, batch normalization (BatchNorm) and Rectified Linear Unit (ReLU) layers.
98. The method of any one of embodiments 94 to 97, wherein the convolutional layers are capable of convolving a 3 by 3 pixel blocks of input images.
99. The method of any one of embodiments 72 to 76, wherein the ReLU layers are capable of applying the function f(x)=max(0,x) to the inputs.
100. The method of any one of embodiments 94 to 99, wherein the BatchNorm layers are capable of normalizing neural network activations.
101. The method of any one of embodiments 94 to 100, wherein the neural network further comprises pooling layers.
102. The method of any one of embodiments 94 to 101, wherein the neural network further comprises dropout layers.
103. The method of any one of embodiments 94 to 102, wherein the neural network further comprises fully connected layers.
104. The method of any one of embodiments 94 to 103, wherein the neural network is capable of executing softmax operation.
105. The method of any one of embodiments 94 to 104, wherein the neural network is pre-trained.
106. The method of embodiment 105, wherein the network is trained to assign a probability score of disease or non-disease by a method comprising the steps of:
   (a) receiving a first training set of input images of organoids having a disease phenotype and a second training set of input images of organoids having a non-disease phenotype;
   (b) comparing probability scores of disease or non-disease for the input images to their true values; and
   (c) updating weights of nodes in the neural network during a backpropagation process through the neural network.
107. The method of embodiment 106, wherein the first training set of input images and the second training set of input images each comprise at least 500 images.
108. The method of embodiment 106 or embodiment 107, wherein the input images are received by the network in a random order.
109. The method of any one of embodiments 106 to 108, which further comprises repeating steps (a) to (c) at least 200 to 800 times, wherein performing steps (a) to (c) comprise 1 epoch.
110. The method of embodiment 109, which comprises about 500 epochs.
111. The method of any one of embodiments 106 to 110, which further comprises augmenting the input images prior to each subsequent epoch.
112. The method of embodiment 111, wherein augmenting comprises rotating, cropping, scaling, or changing the contrast of the images, or a combination of two, three or all four operations.
113. The method of any one of embodiments 106 to 112, which comprises repeating steps (a) to (c) at least five times with different hyperparameters.
114. The method of any one of embodiments 106 to 112, which comprises repeating steps (a) to (c) at least 10 times with different hyperparameters.
115. The method of any one of embodiments 106 to 112, which comprises repeating steps (a) to (c) at least 20 times with different hyperparameters.
116. The method of any one of embodiments 113-115, wherein the hyperparameters comprise the number and type of layers, momentum and learning rate, dropout percentage, number of epochs, or a combination of two, three or all four hyperparameters.
117. The method of any one of embodiments 89 to 97, wherein the neural network comprises a fully connected layer having 512 nodes.
118. The method of any one of embodiments 89 to 98, wherein the final fully connected layer has 2 nodes, reflecting the disease and non-disease phenotypes.
119. The method of any one of embodiments 103 to 118, further comprising:
   (a) culturing a third mammalian cell population of the same cell type(s) as the first cell population under organoid formation conditions that result in an organoid with the disease phenotype;
   (b) culturing a fourth mammalian cell population of the same cell type(s) as the first cell population under organoid formation conditions that result in an organoid without the disease phenotype;
   (c) imaging the organoids formed from the third and fourth mammalian cell populations; and
   (d) analyzing one or more images of the organoid formed from the third mammalian cell population and one or more images of the organoid formed from the fourth mammalian cell population using the neural network to obtain latent vectors for the disease and non-disease phenotypes.
120. The method of embodiment 119, wherein the first and third mammalian cell populations contain one or more mutations that confer the disease phenotype and wherein, other than said one or more mutations, the fourth mammalian cell population is isogenic to the first and third mammalian cell populations.
121. The method of embodiment 119 or embodiment 120, wherein culturing the first mammalian cell population, culturing the third mammalian cell population, and culturing the fourth mammalian cell population are performed concurrently.
122. The method of any one of embodiments 35 to 121, wherein the neural network assigns a probability score of toxicity or non-toxicity to an organoid exposed to a test molecule by a method comprising:
   (a) extracting a fully connected layer upstream of the two last nodes; and
   (b) quantifying a difference between a latent vector associated with the first mammalian cell population that has contacted a test molecule, the latent vector associated with the first cell population that has not contacted a test molecule, and the latent vector associated with the second cell population, to provide a degree of difference with the first mammalian cell population that has contacted a test molecule, latent vector associated with the first cell population that has not contacted a test molecule, and the latent vector associated with the second cell population.
123. The method according to embodiment 122, wherein the degree of difference is calculated by taking the minimum of the difference between the latent vector associated with the first mammalian cell population that has contacted a test molecule, latent vector associated with the first cell population that has not contacted a test molecule, and the latent vector associated with the second cell population.

124. The method according to embodiment 123, wherein the degree of difference is determined across an entire latent space.
125. The method according to embodiment 124, wherein the latent space comprises at least 10 dimensions.
126. The method according to embodiments 124, wherein the latent space comprises at least 100 dimensions.
127. The method according to embodiment 124, wherein the latent space comprises at least 250 dimensions.
128. The method according to embodiment 124, wherein the latent space comprises at least 400 dimensions.
129. The method according to embodiment 124, wherein the latent space comprises at least 500 dimensions.
130. The method according to embodiment 124, wherein the latent space comprises at least 600 dimensions.
131. The method according to embodiment 124, wherein the latent space comprises at least 800 dimensions.
132. The method according to embodiment 124, wherein the latent space comprises at least 1000 dimensions.
133. The method according to any one of embodiments 123-132, wherein the latent space is reduced.
134. The method of embodiment 133, wherein the dimensionality-reducing method is t-distributed stochastic neighbor embedding (t-SNE), or principal component analysis (PCA).
135. The method of embodiment 133 or embodiment 134, which further comprises plotting the probability score of disease or non-disease and the probability score of toxicity or non-toxicity in a graphical format.
136. The method of embodiment 135, wherein the graphical format is an equilateral triangle, the corners of which signify a non-disease phenotype, a disease phenotype, and a toxic phenotype.
137. A system comprising:
    (a) a processor; and
    (b) a non-transient storage medium including processor executable instructions implementing the analyzing step of any of claims 1-19.
138. A system comprising:
    (a) a processor; and
    (b) a non-transient storage medium including processor executable instructions implementing step (c) of any one of embodiments 27-84.
139. A system comprising:
    (a) a processor; and
    (b) a non-transient storage medium including processor executable instructions implementing step (c) of embodiment 27.
140. A non-transient storage medium including processor executable instructions for: receiving organoid images and utilizing a neural network to analyze one or more images of an organoid using a neural network and assign a probability score of disease or non-disease ranging between 0% and 100%.
141. The non-transient storage medium according to embodiment 140, wherein the non-transient storage medium comprises the neural network utilized in the method of any one of embodiments 94-118 and 122-136.
142. A method of training a neural network to analyze one or more images of an organoid and assign a probability score of disease or non-disease ranging between 0% and 100%, said method comprising the steps of:

(a) receiving a first training set of input images of organoids having a disease phenotype and a second training set of input images of organoids having a non-disease phenotype;
(b) comparing probability scores of disease or non-disease for the input images to their true values; and
(c) updating weights of nodes in the neural network during a backpropagation process through the neural network.

143. The method of embodiment 142, wherein the first training set of input images and the second training set of input images each comprise at least 500 images.
144. The method of embodiment 142 or embodiment 143, wherein the input images are received by the network in a random order.
145. The method of any one of embodiments 142 to 144, which further comprises repeating steps (a) to (c) at least 200 times.
146. The method of any one of embodiments 142 to 144, which further comprises repeating steps (a) to (c) at least 400 times.
147. The method of any one of embodiments 142 to 144, which further comprises repeating steps (a) to (c) at least 500 times.
148. The method of any one of embodiments 142 to 144, which further comprises repeating steps (a) to (c) at least 600 times.
149. The method of any one of embodiments 142 to 144, which further comprises repeating steps (a) to (c) at least 800 times
150. The method of any one of embodiments 142 to 144, which further comprises repeating steps (a) to (c) at least 1000 times.
151. The method of embodiment 145, which comprises about 500 epochs.
152. The method of embodiments 145 or 151, which further comprises augmenting the input images prior to each subsequent epoch.
153. The method of embodiment 152, wherein augmenting comprises rotating, cropping, scaling, or changing the contrast of the images, or a combination of two, three or all four operations.
154. The method of any one of embodiments 142 to 153, which comprises repeating steps (a) to (c) at least at least five times with different hyperparameters.
155. The method of any one of embodiments 142 to 153, which comprises repeating steps (a) to (c) at least at least at least 10 times with different hyperparameters.
156. The method of any one of embodiments 142 to 153, which comprises repeating steps (a) to (c) at least at least 20 times with different hyperparameters.
157. The method of embodiment 154, wherein the hyperparameters comprise the number of layers, momentum and learning rate, dropout percentage, number of epochs, or a combination of two, three, or all four hyperparameters.
158. The method of any one of embodiments 142 to 157, which comprises a fully connected layer having 512 nodes.
159. The method of any one of embodiments 142 to 158, wherein the final fully connected layer has 2 nodes, reflecting the disease and non-disease phenotypes.
160. A system comprising:
    (a) an imaging device capable of imaging an organoid;
    (b) a processor configured for:
        (i) receiving organoid images from the imaging device; and (ii) utilizing a neural network to analyze one or more images of the organoid using a neural network and assign a probability score of disease or non-disease ranging between 0% and 100%.

161. The system according to embodiment 160, wherein the neural network is the neural network utilized in the method of any one of embodiments 94-118 and 122-136.

162. A system comprising:
(a) an imaging device capable of imaging an organoid;
(b) a processor configured for:
  (i) receiving organoid images from the imaging device; and
  (ii) training a neural network to analyze one or more images of an organoid and assigning a probability score of disease or non-disease ranging between 0% and 100% according to the methods of any one of embodiments 142-159.

163. A system comprising:
a. an imaging device capable of imaging an organoid;
b. a processor configured for:
  i. receiving organoid images from the imaging device;
  ii. training a neural network to analyze one or more images of an organoid and assigning a probability score of disease or non-disease ranging between 0% and 100% according to the methods of any one of embodiments 142-159; and
  iii. utilizing the neural network to analyze one or more images of the organoid using a neural network and assign a probability score of disease or non-disease ranging between 0% and 100%.

164. A method of determining the toxicity of a test molecule, said method comprising:
a) performing the method, or collecting or obtaining data from the method, according to any one of embodiments 27-136, e.g., such that the data (e.g., image data) produced or collected is represented in a latent space;
b) removing the distance between wild type and disease from the latent space;
c) calculating the distance from the mean vector of the wild type phenotypes and disease phenotype;
d) comparing the distance calculated from step (c) and the standard deviation of the wild type phenotype and disease phenotype; and
e) determining a toxicity value, optionally wherein steps (a) through (e) are performed by an autoencoder, e.g., a convolutional autoencoder.

165. The method according to embodiment 164, wherein determining a toxicity value comprises assigning a probability score of toxicity or non-toxicity ranging between 0% and 100%.

166. The method of embodiment 165, which further comprises assigning the first organoid a probability score of toxicity or non-toxicity ranging between 0% and 100%.

167. The method of embodiment 165 or embodiment 166, which further comprises determining the LC50 of the test molecule.

168. The method of embodiment 167, wherein determining the LC50 of the test molecule comprises repeating the method of embodiment 166 using at least 3 different concentrations of the test molecule and analyzing the probability scores of toxicity or non-toxicity for different concentrations using a nonlinear least-square fit algorithm.

169. The method of any one of embodiments 164 to 168, which further comprises determining the IC50 and LC50 of the test molecule and selecting for further analysis a test molecule that has a greater LC50 than IC50.

170. The method of embodiment 169, wherein the LC50 is at least 10 times greater than the IC50.

171. The method of embodiment 169, wherein the LC50 is at least 100 times greater than the IC50.

172. The method of any one of embodiments 1 to 26, wherein the neural network comprises an autoencoder, optionally wherein the autoencoder is a convolutional autoencoder.

173. The method of any one of embodiments 1 to 26, wherein the classification further comprises a toxicity phenotype.

174. The method of embodiment 173, wherein the toxicity phenotype is assigned by an autoencoder.

175. The method of embodiment 174, wherein the toxicity phenotype is determined by the autoencoder performing (a) through (e) of any one of embodiments 164 to 171.

176. The system of any one of embodiments 137 to 139 and 160 to 164, which comprises an autoencoder configured to assign a toxicity score according to steps (a) through (e) of any one of embodiments 164 to 171.

177. The non-transient storage medium of embodiment 140 or embodiment 141, which is configured to assign a toxicity score by the method of steps (a) through (e) of any one of embodiments 164 to 171.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method for classifying a test organoid, said method comprising the steps of:
(a) imaging a test organoid to provide an organoid image; and
(b) analyzing the organoid image with a trained neural network that has been trained to assign a classification to the test organoid, wherein the classification comprises disease phenotype or non-disease phenotype.

2. The method of claim 1, wherein the cells of the organoid having a disease phenotype comprise one or more mutations that confer the disease phenotype.

3. The method of claim 1, wherein the test organoid comprises cells differentiated from: i) stem cells, ii) pluripotent cells, iii) induced pluripotent cells, iv) human embryonic stem cells, v) adult stem cells, vi) totipotent stem cells, or vii) non-embryonic cell.

4. The method of claim 1, wherein the disease phenotype is a Huntington's disease phenotype.

5. The method of claim 1, further comprising staining the test organoids for one or more markers.

6. The method of claim 5, wherein the one or more markers comprise an organelle marker, a cell differentiation marker, a cell compartment marker, or a combination thereof.

7. The method of claim 5, wherein at least two organoid images of the test organoid are analyzed, each corresponding to a different marker and a different color channel.

8. The method of claim 1, wherein the trained neural network is a neural network trained with a plurality of images of organoids belonging to a non-disease classification and a plurality of images of organoids belonging to a disease classification, wherein said neural network comprises a plurality of layers and a last layer comprising two nodes.

9. A system comprising:
 (a) a processor; and
 (b) a non-transient storage medium including processor executable instructions implementing the analyzing step of claim 1.

10. A method for identifying a test molecule that is biologically active against a disease, comprising:
 (a) culturing a first mammalian cell population under organoid formation conditions to obtain a first organoid, wherein the organoid formation conditions include exposure to a test molecule, and wherein the first mammalian cell population, when cultured under the organoid formation conditions in the absence of a biologically active molecule, results in an organoid with a disease phenotype;
 (b) imaging the first organoid following exposure to the test molecule;
 (c) analyzing one or more images of the first organoid using a neural network that has been trained to assign a probability score of disease or non-disease ranging between 0% and 100%; and
 (d) assigning the first organoid a probability score ranging between 0% and 100%;
 wherein the test molecule is biologically active against the disease if the probability score of the first organoid is greater than a cutoff probability score of non-disease or lower than a cutoff probability score of disease, optionally wherein the first mammalian cell population contains one or more mutations that confer the disease phenotype.

11. The method of claim 10, wherein the neural network has further been trained to assign a probability score of toxicity or non-toxicity ranging between 0% and 100%, and wherein the method optionally further comprises assigning the first organoid a probability score of toxicity or non-toxicity ranging between 0% and 100%.

12. The method of claim 10, which further comprises verifying the accuracy of the neural network, optionally wherein verifying accuracy of the neural network comprises:
 (a) culturing a second mammalian cell population of the same cell type(s) as the first cell population under organoid formation conditions to obtain a second organoid, wherein the second mammalian cell population, when cultured under the organoid formation conditions in the absence of a biologically active molecule, results in an organoid without the disease phenotype;
 (b) imaging the second organoid; and
 (c) assigning the second organoid a probability score ranging between 0% and 100%,
wherein the neural network is deemed to be accurate if the probability score of the second organoid is greater than a cutoff probability score of non-disease or lower than a cutoff probability score of disease.

13. The method of claim 10, wherein the first mammalian cell population encodes a Huntingtin protein with an expanded polyglutamine repeat, optionally wherein the expanded polyglutamine repeat contains 42-150 glutamine residues.

14. The method of claim 10, wherein the probability score is given on a scale of 0 to 1 and/or wherein the cutoff probability score is 95%.

15. A method of screening a collection of test molecules to identify a molecule that is biologically active against a disease, comprising performing the method of claim 10 for each test molecule in the collection, optionally wherein the test molecules are screened individually or screened in pools.

16. A system comprising:
 (a) a processor; and
 (b) a non-transient storage medium including processor executable instructions implementing step (c) of claim 10.

17. A method of determining the toxicity of a test molecule, said method comprising:
 a) performing the method of claim 10;
 b) removing the distance between wild type and disease from the latent space;
 c) calculating the distance from the mean vector of the wild type phenotypes and disease phenotype;
 d) comparing the distance calculated from step (c) and the standard deviation of the wild type phenotype and disease phenotype; and
 e) determining a toxicity value.

18. The method of claim 10, which further comprises verifying the accuracy of the neural network, optionally wherein verifying accuracy of the neural network comprises:
 (a) culturing a third mammalian cell population of the same cell type(s) as the first cell population under organoid formation conditions to obtain a third organoid, wherein the third mammalian cell population, when cultured under the organoid formation conditions in the absence of a biologically active molecule, results in an organoid with the disease phenotype;
 (b) imaging the third organoid; and
 (c) assigning the third organoid a probability score ranging between 0% and 100%,
wherein the neural network is deemed to be accurate if the probability score of the third organoid is lower than a cutoff probability score of non-disease or greater than a cutoff probability score of disease.

19. A non-transient storage medium including processor executable instructions for: (a) receiving organoid images and (b) utilizing a neural network to (i) analyze one or more images of an organoid using a neural network and (ii) assign a probability score of disease or non-disease ranging between 0% and 100%.

20. A method of training a neural network to analyze one or more images of an organoid and assign a probability score of disease or non-disease ranging between 0% and 100%, said method comprising the steps of:
 (a) receiving a first training set of input images of organoids having a disease phenotype and a second training set of input images of organoids having a non-disease phenotype;
 (b) comparing probability scores of disease or non-disease for the input images to their true values; and
 (c) updating weights of nodes in the neural network during a backpropagation process through the neural network.

21. A system comprising:
 (a) an imaging device capable of imaging an organoid;
 (b) a processor configured for:

(i) receiving organoid images from the imaging device; and
(ii) training a neural network to analyze one or more images of an organoid and assigning a probability score of disease or non-disease ranging between 0% and 100% according to the method of claim 20.

22. A system comprising:
(a) an imaging device capable of imaging an organoid;
(b) a processor configured for:
   (i) receiving organoid images from the imaging device; and
   (ii) utilizing a neural network to analyze one or more images of the organoid using a neural network and assign a probability score of disease or non-disease ranging between 0% and 100%.

23. A system comprising:
(a) an imaging device capable of imaging an organoid;
(b) a processor configured for:
   i. receiving organoid images from the imaging device;
   ii. training a neural network to analyze one or more images of an organoid and assigning a probability score of disease or non-disease ranging between 0% and 100% according to the method of claim 20; and
   iii. utilizing the neural network to analyze one or more images of the organoid using a neural network and assign a probability score of disease or non-disease ranging between 0% and 100%.

* * * * *